(12) United States Patent
Ferrandez et al.

(10) Patent No.: US 8,841,088 B2
(45) Date of Patent: Sep. 23, 2014

(54) METHOD FOR MRNA STABILIZATION

(75) Inventors: Abel Ferrandez, Basel (CH); John B. Perkins, Wassenaar (NL); Michèle Schaber, Basel (CH)

(73) Assignee: DSM IP Assets B.V., Heerlen (NL)

( * ) Notice: Subject to any disclaimer, the term of this patent is extended or adjusted under 35 U.S.C. 154(b) by 1060 days.

(21) Appl. No.: 12/095,985

(22) PCT Filed: Dec. 1, 2006

(86) PCT No.: PCT/EP2006/011547
§ 371 (c)(1),
(2), (4) Date: Jul. 3, 2008

(87) PCT Pub. No.: WO2007/065602
PCT Pub. Date: Jun. 14, 2007

(65) Prior Publication Data
US 2008/0299662 A1 Dec. 4, 2008

(30) Foreign Application Priority Data
Dec. 5, 2005 (EP) .................................... 05026475

(51) Int. Cl.
*C12P 21/00* (2006.01)
*C12N 15/67* (2006.01)
*C07H 21/02* (2006.01)
*C07H 21/04* (2006.01)

(52) U.S. Cl.
CPC ...................................... *C12N 15/67* (2013.01)
USPC ........................ 435/69.1; 435/91.41; 536/23.1

(58) Field of Classification Search
None
See application file for complete search history.

(56) References Cited

PUBLICATIONS

Hambreus et al., Microbiology, 148, 1795-1803 (2002).*
Bricker et al. "Importance of a 5' stem-loop for longevity of papa mRNA in *Escherichia coli*" Journal of Bacteriology, vol. 181, No. 11, pp. 3587-3590 (Jun. 1999).
Carrier et al. "Engineering mRNA stability in *E. coli* by the addition of synthetic hairpins using a 5' cassette system" Biotechnology and Bioengineering, vol. 55, No. 3, pp. 577-580 (1997).
Carrier et al. "Controlling messenger RNA stability in bacteria: Strategies for engineering gene expression" Biotechnology Progress, vol. 13, No. 6, pp. 699-708 (Nov. 1997).
Hambraeus et al. "A 5' stem-loop and ribosome binding but not translation are important for the stability of *Bacillus subtilis* aprE leader mRNA" Microbiology, vol. 148, No. 6, pp. 1795-1803 (Jun. 2002).
Homuth et al. "Post-transcriptional Regulation of the *Bacillus subtilis* dnak operon" Molecular Microbiology, vol. 32, No. 6, pp. 1183-1197 (Jun. 1999).
Meinken et al. "Expression of the glycolytic gapA operon in *Bacillus subtilis*: Differential syntheses of proteins encoded by the operon" Microbiology, vol. 149, No. pt. 3, pp. 751-761 (Mar. 2003).
Smolke et al. "Controlling the metabolic flux through the carotenoid pathway using directed mRNA processing and stabilization" Metabolic Engineering, vol. 3, No. 4, pp. 313-321 (Oct. 2001).
International Search Report for PCT/EP2006/011547, mailed Mar. 28, 2007.
Written Opinion for PCT/EP2006/011547, mailed Mar. 28, 2007.
Bricker et al. "Importance of a 5' stem-loop for longevity of papA mRNA in *Escherichia coli*" J. Bacteriol. vol. 181:3587-3590 (Jun. 1999).
Carrier et al. "Engineering mRNA stability in *E. coli* by the addition of synthetic hairpins using a 5' cassette system" Biotechnol. Bioeng. vol. 55, No. 3, pp. 577-580 (Aug. 1997).
Carrier et al. "Controlling messenger RNA stability in bacteria: Strategies for engineering gene expression" Biotechnol. Prog. vol. 13, No. 6, pp. 699-708 (Nov.-Dec. 1997).
Hambraeus et al. "A 5' stem-loop and ribosome binding but not translation are important for the stability of *Bacillus subtilis* aprE leader mRNA" Microbiol. vol. 148, No. 6, pp. 1795-1803 (Jun. 2002).
Homuth et al. "Post-granscriptional regulation of the *Bacillus subtilis* dnaK operon" Mol. Microbiol. vol. 32, No. 6, pp. 1183-1197 (Jun. 1999).
Meinken et al. "Expression of the glycolytic gapA operon in *Bacillus subtilis*: Differential syntheses of proteins encoded by the operon" Microbiol. vol. 149, pt. 3, pp. 751-761 (Mar. 2003).
Smolke et al. "Controlling the metabolic flux through the carotenoid pathway using directed mRNA processing and stabilization" Metabolic Eng. vol. 3, No. 4, pp. 313-321 (Oct. 2001).

\* cited by examiner

*Primary Examiner* — Nancy T Vogel
(74) *Attorney, Agent, or Firm* — Nixon & Vanderhye P.C.

(57) ABSTRACT

A method to increase the production of a desired chemical compound in a microorganism by introduction of a DNA sequence at the 5' end of the encoding DNA gene sequence capable of forming a stem loop and capable of increasing the stability of mRNA transcripts from one or more genes, thus stabilized mRNAs, corresponding DNA sequences and microorganisms.

9 Claims, No Drawings

SEQUENCE LISTING

```
<160> NUMBER OF SEQ ID NOS: 49

<210> SEQ ID NO 1
<211> LENGTH: 2131
<212> TYPE: DNA
<213> ORGANISM: Bacillus subtilis

<400> SEQUENCE: 1
atgaaccagt taatacaagc tcaaaaaaaa ttattgcctg atcttctgct cgttatgcaa        60
aagaggtttg aaatcttgca gtatatcagg ctgacagaac ccatcgggcg aagaagcctg       120
```

```
tctgccagtc tcggaatcag cgagcgtgtg ctgaggggcg aggttcagtt tttaaaggaa      180
cagaacctgg tcgatattaa gacaaacggc atgacattga cagaagaggg ctatgaactg      240
ctttctgttt tggaagatac gatgaaagat gttttaggtt tgactctttt ggaaaagaca      300
ttaaaagaac gtttaaatct aaaggatgcc attatcgtat ccggagacag cgatcaatcc      360
ccatgggtca aaaagaaat gggaagagcg gctgtcgcat gtatgaaaaa agattttca       420 ggcaaaaata tcgtcgctgt aactggcggt acgacaattg aagctgtcgc cgaaatgatg      480
acgccggatt ctaaaaaccg cgagcttttg tttgtgcctg caagaggcgg tttaggcgaa      540
gacgtgaaaa accaggcgaa caccatatgc gcgcatatgg cggagaaggc ttcaggcact      600
taccggcttt tgtttgttcc gggacagctg tcacaaggcg cctattcatc tattattgaa      660
gagccttctg tcaaagaggt gctgaacacc attaaatcag cgagtatgct ggttcacgga      720
atcggcgaag ctaaaactat ggctcagcgc agaaacacgc ctttagaaga tttaaagaaa      780
atagatgata cgacgcggt gacggaagcg ttcggctact attttaacgc ggacggcgaa      840
gtggttcaca aagtgcattc tgtcggaatg cagctggatg acatagacgc catccccgat      900
attattgcgg tagcgggcgg atcatcaaaa gccgaagcga tcgaggctta ctttaaaaag      960
ccacgcaaca cggttctcgt cacagacgaa ggagccgcaa agaagttatt aagggatgaa     1020
taatccctca atataaatat ctctcactta tttaaggag gaaacaatca tggcagtaaa     1080
agtcggtatt aacggttttg gtcgtattgg acgtaacgta ttccgcgcag cattaaacaa     1140
tcctgaagtt gaggtagtag cggttaacga tttaacagat gctaacatgc tggctcacct     1200
tttacaatat gattctgtac acggaaaatt agacgctgaa gtttcagttg acggtaacaa     1260
ccttgttgtt aacggcaaaa caattgaagt ttctgcagaa cgcgatcctg ctaaacttag     1320
ctggggcaaa caaggcgttg aaatcgtagt tgaatctact ggtttcttca aaaacgcgc      1380 agacgctgcg aaacacttag aagctggcgc gaaaaaagta atcatctctg ctcctgctaa     1440
cgaagaagat atcacaatcg ttatgggtgt taacgaagat aaatacgatg cggctaacca     1500
cgatgttatc tctaacgcat cttgcacaac aaactgcctt gcgccgtttg caaaagtact     1560
taacgataaa ttcggcatca acgcggtat gatgacaact gttcactctt acacaaacga     1620
tcagcaaatc cttgatcttc cgcacaaaga ctaccgtcgt gcgcgtgcag cagctgaaaa     1680
catcatccca acatcaactg gtgctgctaa agcagtttct ctagttcttc ctgaactaaa     1740
aggcaaactg aacggtggag caatgcgtgt tccaactcca acgtttctc tagttgactt      1800 ggttgctgaa ctgaaccaag aagtaacagc tgaagaagta aacgcagctc ttaaagaagc     1860
ggctgaaggc gaccttaaag gaatccttgg ctacagcgaa gagccattag tttctggcga     1920
ctacaacgga aacaaaaact cttctacaat cgatgctctt tctacaatgg ttatggaagg     1980
cagcatggta aaagtaatct cttggtacga taacgaaagc ggctactcta accgcgttgt     2040
tgaccttgca gcttacatcg caaaaaaagg tctttaattt atagctgaaa aaggacctga     2100
cttggttctt tcgaatagaa gcgctataat g                                   2131
```

<210> SEQ ID NO 2
<211> LENGTH: 167
<212> TYPE: DNA
<213> ORGANISM: Bacillus subtilis

<400> SEQUENCE: 2

```
ccgatattat tgcggtagcg ggcggatcat caaaagccga agcgatcgag gcttacttta      60
aaaagccacg caacacggtt ctcgtcacag acgaaggagc cgcaaagaag ttattaaggg     120
atgaataatc cctcaatata aatatctctc acttatttaa aggagga                   167
```

<210> SEQ ID NO 3
<211> LENGTH: 1664
<212> TYPE: DNA
<213> ORGANISM: Bacillus subtilis

<400> SEQUENCE: 3

```
atgttaacaa atcgtcagct gctgatcctt caggttataa tcaacgattt tattaaatcg      60
gcacagccgg tgggatcaag aactctttcg aaaaaagatg aaatcacatt tagctctgca     120
acaataagaa acgagatggc tgacttggag gaattgggct ttattgaaaa aacccattca     180
tcctcaggac gtgttccgtc agaaaaaggg tatcggtact atgttgacca tttgctgtca     240
cccgtcaaat tgacgaaaag cgacctggac caaatccact cgatcttcaa agagaaaatt     300
ttcgagctgg agaagacagt tcaaaaatca gcgcaaattt tgtccgatct gacgaattac     360
acatccatcg tactcgggcc gaagttgagt gagaattacc ttaaacagat tcaaatcatt     420
ccgattcagc ctgatatggc ggtagcgatt ctcgttacca atacggggca tgtggaaaac     480
aaaacgatta actttccgac caaaatggat ctgtctgata ttgaaaaact ggtaaatata     540
ctgaacgacc gtttaagcgg cgttccaatg gatgaactga atgagcgcat atttaaagaa     600
gttgtcatgt acctaagaca gcacattaaa aactatgaca atatactcga cgcgcttcgt     660
tcaacctttc attccacaaa tcacgttgaa aagttgtttt ttggcgggaa aatcaatatg     720
ctgaaccagc ctgagttcca tgatatcacc cgagttcggt cgctgctttc attaattgag     780
aaagaacagg atgttttaaa gctggttcaa tccccgcaca cgggaatttc gattaaaatc     840
ggaaaagaaa cgactatga agagatggaa aattgcagtc tgattacggc ttcttattcc     900
gtagaccaga agcagatcgg ctcaattgcg attatcggcc cgacccgcat gaattattcc     960
agggttgtca gcctgcttca gcatgtgact tcggacttgt caaaagcatt aacaagtctg    1020
tatgatgaat aagggaattt tggcaaattt tatcgaaggg cagcacctgt ccttctcctt    1080
acactttgag ggaggtgaac acaatgtcag aagaaaaaca aaccgttgaa caaaacgaaa    1140
cagaagagca agaaatcatt gaagaacaag ctgccgctga tgaacagcag gaagaaacaa    1200
atgaaagcga acttcttcaa aaccaaatta acgaattgca aggtttgctt gaggaaaaag    1260
aaaacaaact tttgcgtgtt caagcagact ttgaaaacta taaacgacgc agccgtttag    1320
agatggaagc gtcccaaaaa taccgttctc aaaatatcgt gactgatttg ctgccggctc    1380
ttgacagttt tgaacgagcg cttcaggttg aagccgacaa tgaacagacg aaaagtttgc    1440
tccagggaat ggaaatggtc caccgtcagc tcgtagaagc cttgaaaaaa gaaggcgtcg    1500
aagccatcga agctgtaggg caggaatttg atcctaatct gcaccaagct gttatgcagg    1560
ctgaagacga aaactacggc tccaacattg ttgttgagga aatgcaaaaa ggctataagc    1620
tgaaggatcg cgtcattcgc ccttccatgg tcaaagtgaa tcaa                     1664
```

<210> SEQ ID NO 4
<211> LENGTH: 101
<212> TYPE: DNA
<213> ORGANISM: Bacillus subtilis

<400> SEQUENCE: 4

```
ctgtatgatg aataagggaa ttttggcaaa ttttatcgaa gggcagcacc tgtccttctc    60
cttacacttt gagggaggtg aacacaatgt cagaagaaaa a                       101
```

<210> SEQ ID NO 5
<211> LENGTH: 8566
<212> TYPE: DNA
<213> ORGANISM: Bacillus subtilis

<400> SEQUENCE: 5

```
gcaagatatc attaatgtat gccgagggaa caagagaagt gcctatccga aattgaaatg    60
gattgcaaga tgatctgtca gactcaatcc atatacgaac catatcgtgt tataaaatct   120
tccatgttta tataaaatta ataattctg gtgtattctt gatagattaa taaaaaaatt    180
ataaaaactt ttaacatttg caattccttt tgtaccaata atgaaagcgt atacaatata   240
gattgattaa tcaaaattgt ctaataattt taaaaaatgc tgttgacact gcgtccaaag   300
cggcgtaata tgagttcaac aaaagacaac agtcccgata ttattgcggt agcgggcgga   360
tcatcaaaag ccgaagcgat cgaggcttac tttaaaaagc cacgcaacac ggttctcgtc   420
acagacgaag gagccgcaaa gaagttatta agggatgaat aatccctcaa tataaatatc   480
tctcacttat ttaaggagg agctagcatg ggactaatg tacaggtgga ttcagcatct    540
gccgaatgta cacagacgat gagcggagca ttaatgctga ttgaatcatt aaaaaaagag   600
aaagtagaaa tgatcttcgg ttatccgggc ggggctgtgc ttccgattta cgataagcta   660
tacaattcag ggttggtaca tatccttccc cgtcacgaac aaggagcaat tcatgcagcg   720
gagggatacg caagggtctc cggaaaaccg ggtgtcgtca ttgccacgtc agggccggga   780
gcgacaaacc ttgttacagg ccttgctgat gccatgattg attcattgcc gttagtcgtc   840
tttacagggc aggtagcaac ctctgtaatc gggagcgatg catttcagga agcagacatt   900
ttagggatta cgatgccagt aacaaaacac agctaccagg ttcgccagcc ggaagatctg   960
ccgcgcatca ttaaagaagc gttccatatt gcaacaactg gaagacccgg acctgtattg  1020
attgatattc cgaaagatgt agcaacaatt gaaggagaat tcagctacga tcatgagatg  1080
aatctcccgg gataccagcc gacaacagag ccgaattatt tgcagatccg caagcttgtg  1140
gaagccgtga gcagtgcgaa aaaaccggtg atcctggcgg gtgcgggcgt actgcacgga  1200
aaagcgtcag aagaattaaa aaattatgct gaacagcagc aaatccctgt ggcacacacc  1260
cttttgggc tcggaggctt cccggctgac catccgcttt tcctagggat ggcgggaatg  1320
cacggtactt atacagccaa tatggccctt catgaatgtg atctattaat cagtatcggc  1380
gcccgttttg atgaccgtgt cacaggaaac ctgaaacact tgccagaaa cgcaaagata  1440
gcccacatcg atattgatcc agctgaaatc ggaaaaatca tgaaaacaca gattcctgta  1500
gtcggagaca gcaaaattgt cctgcaggag ctgatcaaac aagacggcaa acaaagcgat  1560
tcaagcgaat ggaaaaaaca gctcgcagaa tggaaagaag agtatccgct ctggtatgta  1620
gataatgaag aagaaggttt taaacctcag aaattgattg aatatattca tcaatttaca  1680
aaaggagagg ccattgtcgc aacgatgta ggccagcatc aaatgtggtc agcgcaattt  1740
tatccgttcc aaaaagcaga taatgggtc acgtcaggcg acttggaac gatgggattc   1800
ggtcttccgg cggcgatcgg cgcacagctg gccgaaaaag atgctactgt tgtcgcggtt  1860
gtcggagacg gcggattcca aatgacgctt caagaactcg atgttattcg cgaattaaat  1920
cttccggtca aggtagtgat tttaaataac gcttgtctcg gaatggtcag acagtggcag  1980
```

```
gaaattttct atgaagaacg ttattcagaa tctaaattcg cttctcagcc tgacttcgtc    2040
aaattgtccg aagcatacgg cattaaaggc atcagaattt catcagaagc ggaagcaaag    2100
gaaaagctgg aagaggcatt aacatcaaga gaacctgttg tcattgacgt gcgggttgcc    2160
agcgaagaaa aagtattccc gatggtggct ccggggaaag ggctgcatga atggtgggg    2220 gtgaaacctt gaaaagaatt atcacattga ctgtggtgaa ccgctccggg gtgttaaacc    2280
ggatcaccgg tctattcaca aaaaggcatt acaacattga aagcattaca gttggacaca    2340
cagaaacagc cggcgtttcc agaatcacct tcgtcgttca tgttgaaggt gaaaatgatg    2400
ttgaacagtt aacgaaacag ctcaacaaac agattgatgt gctgaaagtc acagacatca    2460
caaatcaatc gattgtccag agggagctgg ccttaatcaa ggttgtctcc gcaccttcaa    2520
caagaacaga gattaatgga atcatagaac cgtttagagc ctctgtcgtt gatgtcagca    2580
gagacagcat cgttgttcag gtgacaggtg aatctaacaa aattgaagcg cttattgagt    2640
tattaaaacc ttatggcatt aaagaaatcg cgagaacagg tacaacggct tttgcgaggg    2700
gaaccagcaa aaggcgtcat ccaataaaac aatatctatt gtataaaaca taacaaggga    2760
gagattgaaa tggtaaaagt atattataac ggtgatatca aagagaacgt attggctgga    2820
aaaacagtag cggttatcgg gtacggttcg caaggccacg cacatgccct gaaccttaaa    2880
gaaagcggag tagacgtgat cgtcggtgtt agacaaggaa aatctttcac tcaagcccaa    2940
gaagacggac ataaagtatt ttcagtaaaa gaagcggcag cccaagccga aatcatcatg    3000
gttctgcttc cggatgagca gcagcaaaaa gtatacgaag ctgaaatcaa agatgaattg    3060
acagcaggaa aatcattagt attcgctcat ggatttaacg tgcatttcca tcaaattgtt    3120
cctccggcgg atgtagatgt attcttagtg gcccctaaag gcccgggaca cttggtaaga    3180
agaacatatg agcaaggagc tggcgtacct gcattgttcg caatctatca agatgtgact    3240
ggagaagcaa gagacaaagc cctcgcttat gctaaaggaa tcggcggcgc aagagcgggc    3300
gtattagaaa cgacatttaa agaagaaaca gaaacagatt tgttcggtga gcaagcagtt    3360
ctttgcggcg gattaagcgc gcttgtcaaa gccggatttg aaaccttaac tgaagcaggt    3420
tatcagcctg aacttgcata cttcgagtgt cttcatgagc tgaaattaat cgtagacctt    3480
atgtacgaag aaggacttgc aggaatgaga tattcaatct ctgacacagc acagtgggga    3540
gatttcgtat caggccctcg cgttgtggac gccaaagtaa aagaatctat gaagaagta    3600 ttaaaagata tccaaaacgg tacattcgca aaagagtgga tcgtcgaaaa ccaagtaaac    3660
cgtcctcgtt tcaacgctat caatgcaagc gagaacgaac atcaaatcga agtagtggga    3720
agaaagcttc gtgaaatgat gccgtttgtg aaacaaggca agaagaagga agcggtggtc    3780
tccgttgcgc aaaattaatt ttttcgatac gacgcttcgt gatggtgaac agtcccctgg    3840
agtgaacttg aatacacagg agaaacttgc catagctaag cagctcgaaa gactcggggc    3900
agacatcatt gaagcgggat ttcccgcttc gtcccgaggt gacttttag ctgttcagga    3960 aatcgcaaga accattaaaa attgttcagt aactggtctg gcccgttgtg taaaaggtga    4020
tattgatgct gcttgggaag cgttaaagga tggcgctcaa ccaagaattc atgtatttat    4080
cgcgacatcg gacattcatt tgaagcacaa gctgaaaatg acacgtgaac aagtcattga    4140
aagagcagtt ggaatggtga atacgcaaa agaacgtttt ccgattgtgc aatggtcagc    4200
tgaagatgcc tgccgcactg aactgccgtt tctagcagaa atcgtcgaga aagtgattga    4260
cgcaggcgcc agtgttatca atcttccgga cactgtcggc tacctggccc cggcggaata    4320
cggaaatatc tttaaatata tgaaagaaaa cgttccgaac attcacaaag caaagctttc    4380
```

```
agcccactgt catgatgatt tgggaatggc agtcgcaaac tctcttgctg cgattgaaaa    4440
tggcgctgat caaatcgaat gcgctgtgaa cgggatcggt gaaagagccg gaaacgcggc    4500
attagaggaa attgccgtag ccctccatac cagaaaagat ttctaccaag tcgaaacagg    4560
tattacgctg aacgagatta agagaacaag tgatttagta agcaaactga caggcatggc    4620
tgtcccgcgc aacaaagcgg ttgttggaga taatgcattt gctcatgaat caggcatcca    4680
tcaggacggc tttttaaagg aaaaatcgac ttatgaaatt atttcaccgg agcttgtcgg    4740
cgtaaccgca gatgcgcttg tcctaggtaa acattccgga cgccacgcat ttaaagaccg    4800
gctgactgct ttaggattcc aatttgacag tgaagagatt aataaattct ttacgatgtt    4860
caaagagttg actgagaaga aaaagaaat cactgatgag gatcttgttt ctcttatttt     4920
agaagaaaaa gtaacagatc gcaagattgg gtatgaattc ttttctctgc aagtacatta    4980
cggaacaagt caggtcccta cggctactct atctttgaaa aatcaagaaa cgcacagct     5040 tattcaggaa gctgcaactg gagctggaag cgtggaagca atctacaata cgcttgagcg    5100
ctgcatcgat aaggatgtgg agctcttaga ctaccgcatt cagtctaata gaaaaggcga    5160
agatgcattt gcccaggtgt atgtaagagt tttggtgaac ggaaaagaat cagcagggcg    5220
gggcatagcg caagacgtat tagaagcatc agcgaaagcc tatttgaacg cagtaaaccg    5280
tcaattggtt ttccagtcga atatgagcgg attgaaaaac cacacagctg tcggatcata    5340
aaagaaagga gaacggttaa cttgaagaaa cgtattgctc tattgcccgg agacgggatc    5400
ggccctgaag tattagaatc agcgacagac gtactgaaaa gtgttgccga acgctttaac    5460
catgaatttg aatttgaata tggcctgatt ggaggggcgg ctattgatga acatcataac    5520
cccctcccgg aggaaaccgt tgctgcttgt aaaaatgcag acgcgatatt gcttggtgct    5580
gtcggcggac cgaaatggga tcaaaacctt tcggaactga accggaaaa agggctgctc     5640 agcatcagaa aacagcttga tttgtttgcg aatttgcggc ctgtgaaggt atttgaaagc    5700 cttctctgacc gttcgccttt gaaaaaagaa tatatagata atgttgattt cgttatcgtt    5760
cgtgagctca caggcggctt gtatttcggc cagccgagca acgttatgt aaacactgaa     5820 ggtgagcagg aagcagtaga tacactgttt tataagcgaa cggaaattga acgagtgatc    5880
agagagggct tcaaaatggc ggcagccaga aaaggcaaag tgacctctgt agataaagcg    5940
aatgttcttg aatcaagccg gctgtggcgt gaagtggctg aggacgttgc acaagaattt    6000
cctgatgtga agcttgagca catgcttgtg gataacgcgg ccatgcagct aatttatgca    6060
ccgaatcaat ttgatgtcgt ggtgactgaa atatgttcg gtgatatttt aagcgatgaa     6120
gcgtccatgc ttacaggctc gctcggaatg ctcccgtcag ccagcctatc aagctctggc    6180
cttcatctgt ttgaacctgt tcatggctcc gcgcctgata ttgccggtaa agggatggca    6240
aatccgttcg cagccatatt gtcagcggca atgcttttga aacatctttt cgggcttgaa    6300
gaggaagcga agctgtaga agatgcggta aacaaagtct tggcttctgg aaaaagaaca    6360
agagacttgg cacggagtga agagttcagc agcactcagg ccattacaga ggaagttaag    6420
gcagcaatca tgagtgaaaa tacaatttct aatgtgtgac agcttacgtt aagcggtctt    6480
agctctaggt agagggagga aataaaagat gatgcctcga acaatcatcg aaaagatttg    6540
ggatcagcat attgtaaaac atggtgaggg aaagccggat cttctctata ttgatttgca    6600
cctcattcat gaggtgacgt ctcctcaggc atttgaaggc ttgagacaaa agggaagaaa    6660
ggtcagaaga ccccaaaaca catttgcgac aatggaccac aacatcccga ctgtcaatcg    6720
```

```
ttttgagata aaggatgaag ttgcgaaacg ccaggtaacg gcgcttgaaa gaaactgtga    6780
ggaatttggc gtgcgccttg ccgatcttca cagtgtggat caagggattg tccatgtcgt    6840
cggacctgaa ctaggcttaa cgcttccagg aaaacgatt  gtgtgcggtg acagtcatac    6900
atcaacacat ggcgctttcg gcgctcttgc atttggaatc gggacgagtg aagttgaaca    6960
tgtcctttcc acacagacac tttggcagca gcgtccaaaa acacttgaag tgcgcgtaga    7020
tggaacgctt caaaaagggg taacggcaaa ggatgtcatc cttgctgtca tcggcaaata    7080
cggtgtgaaa ttcggcacag gctacgtcat tgaatacact ggggaagtat tcagaaatat    7140
gacgatggat gaacgaatga ctgtttgtaa catgtcaatt gaagcaggag caagagcagg    7200
tttgattgca cctgacgagg tgacgtttga atattgcaaa aatcgcaagt acacgccaaa    7260
aggcgaagaa tttgacaagg ccgtagagga tggaaggcg  ctgcgcacag acccgggcgc    7320
tgtttacgat aaatctatcg tccttgacgg caacaaaatt tcccctatgg tgacatgggg    7380
cattaacccg ggaatggttc ttcctgtcga ttctgaagtt cctgcgccgg aaagcttttc    7440
tgcagaagac gataaaaaag aagcgattcg tgcttatgaa tatatgggat tgactcctca    7500
ccaaaaaatt gaagacatta agtggagca  cgtatttatc ggttcctgca caaattcccg    7560
catgactgac cttcgacagg ctgctgacat gatcaaaggg aagaaggtag ctgacagcgt    7620
aagggccatc gtcgtgcccg gatcccaaag cgtgaagctt caggctgaaa agaagggct    7680
tgaccagatt ttcttggaag ctggatttga atggagagag tcaggctgca gcatgtgttt    7740
gagtatgaat aatgatgttg ttcctgaggg agagcgctgt gcatcaacct ctaaccgcaa    7800
cttcgagggc agacaaggaa aaggtgcaag aacacatctc gtcagcccgg caatggctgc    7860
gatggctgcc attcacggac acttcgttga tgtcagaaag ttttatcagg aaaaaacagt    7920
tgtgtaagga gtgcgcgaga tggaaccttt gaaatcacat acggggaaag cagccgtatt    7980
aaatcggatc aatgtggata cagaccagat tattcctaag caattttga  agaggattga    8040
aagaacaggc tacggacgtt ttgcattctt tgactggaga tatgatgcga atggtgaacc    8100
gaaccctgaa tttgaattaa accagcctgt ttatcaagga gcttccattt taatagcagg    8160
agaaaacttc ggctgcgggt catcgcgtga acacgctccg tgggcacttg atgattatgg    8220
gtttaaaatt atcattgcgc cgtcattcgc tgatattttc catcagaact gctttaaaaa    8280
cggcatgctt ccgatccgca tgccatatga caattggaaa cagcttgtcg gccagtatga    8340
aaaccagtca ttgcaaatga ctgttgacct tgaaaatcag ctgattcatg acagtgaagg    8400
caatcaaatt tcatttgaag ttgatccgca ttggaaagag atgctgatca acggatatga    8460
tgaaatttca ttaacgctgc tgctggaaga tgaaatcaag caatttgaat cacaaagaag    8520
ctcttggctt caagcctgaa aaagcggccg gtatttgtcc ggcggc                  8566
```

<210> SEQ ID NO 6
<211> LENGTH: 1963
<212> TYPE: DNA
<213> ORGANISM: Bacillus subtilis

<400> SEQUENCE: 6

```
caatattaat agttggaggg ttcaaatcga aagaaagcta tataaatata aaaacacgaa      60
agaacaaaac aaggtgaggg cggcctgtat ttatcttatt tgcaaaaaca gcccataaat     120
aaactgaaaa ttgtcaaaat aaaatccaat caaacaattg aagctttctg tatgatgaat     180
aagggaattt tggcaaattt tatcgaaggg cagcacctgt ccttctcctt acactttgag     240
ggaggtgaac acaatgtcag aagaaaaaga atttaggagg atcaccatgg cagaattacg     300
```

| | | | | |
|---|---|---|---|---|
| cagtaatatg | atcacacaag | gaatcgatag | agctccgcac | cgcagtttgc | ttcgtgcagc | 360 |
| aggggtaaaa | gaagaggatt | tcggcaagcc | gtttattgcg | gtgtgtaatt | catacattga | 420 |
| tatcgttccc | ggtcatgttc | acttgcagga | gtttgggaaa | atcgtaaaag | aagcaatcag | 480 |
| agaagcaggg | ggcgttccgt | ttgaatttaa | taccattggg | gtagatgatg | gcatcgcaat | 540 |
| ggggcatatc | ggtatgagat | attcgctgcc | aagccgtgaa | attatcgcag | actctgtgga | 600 |
| aacggttgta | tccgcacact | ggtttgacgg | aatggtctgt | attccgaact | gcgacaaaat | 660 |
| cacaccggga | atgcttatgg | cggcaatgcg | catcaacatt | ccgacgattt | tgtcagcgg | 720 |
| cggaccgatg | gcggcaggaa | gaacaagtta | cgggcgaaaa | atctcccttt | cctcagtatt | 780 |
| cgaaggggta | ggcgcctacc | aagcagggaa | aatcaacgaa | aacgagcttc | aagaactaga | 840 |
| gcagttcgga | tgcccaacgt | gcgggtcttg | ctcaggcatg | tttacggcga | actcaatgaa | 900 |
| ctgtctgtca | gaagcacttg | gtcttgcttt | gccgggtaat | ggaaccattc | tggcaacatc | 960 |
| tccggaacgc | aaagagtttg | tgagaaaatc | ggctgcgcaa | ttaatggaaa | cgattcgcaa | 1020 |
| agatatcaaa | ccgcgtgata | ttgttacagt | aaaagcgatt | gataacgcgt | tgcactcga | 1080 |
| tatggcgctc | ggaggttcta | caaataccgt | tcttcatacc | cttgcccttg | caaacgaagc | 1140 |
| cggcgttgaa | tactctttag | aacgcattaa | cgaagtcgct | gagcgcgtgc | cgcacttggc | 1200 |
| taagctggcg | cctgcatcgg | atgtgtttat | tgaagatctt | cacgaagcgg | gcggcgtttc | 1260 |
| agcggctctg | aatgagcttt | cgaagaaaga | aggagcgctt | catttagatg | cgctgactgt | 1320 |
| tacaggaaaa | actcttggag | aaaccattgc | cggacatgaa | gtaaaggatt | atgacgtcat | 1380 |
| tcacccgctg | gatcaaccat | tcactgaaaa | gggaggcctt | gctgttttat | tcggtaatct | 1440 |
| agctccggac | ggcgctatca | ttaaaacagg | cggcgtacag | aatgggatta | caagacacga | 1500 |
| agggccggct | gtcgtattcg | attctcagga | cgaggcgctt | gacggcatta | tcaaccgaaa | 1560 |
| agtaaaagaa | ggcgacgttg | tcatcatcag | atacgaaggg | ccaaaaggcg | gacctggcat | 1620 |
| gccggaaatg | ctggcgccaa | catcccaaat | cgttggaatg | ggactcgggc | caaaagtggc | 1680 |
| attgattacg | gacggacgtt | tttccggagc | ctcccgtggc | ctctcaatcg | gccacgtatc | 1740 |
| acctgaggcc | gctgagggcg | ggccgcttgc | ctttgttgaa | aacggagacc | atattatcgt | 1800 |
| tgatattgaa | aaacgcatct | tggatgtaca | agtgccagaa | gaagagtggg | aaaaacgaaa | 1860 |
| agcgaactgg | aaaggttttg | aaccgaaagt | gaaaaccggc | tacctggcac | gttattctaa | 1920 |
| acttgtgaca | agtgccaaca | ccggcggtat | tatgaaaatc | tag | | 1963 |

<210> SEQ ID NO 7
<211> LENGTH: 23
<212> TYPE: DNA
<213> ORGANISM: Artificial Sequence
<220> FEATURE:
<223> OTHER INFORMATION: PCR primer

<400> SEQUENCE: 7
gcgactccag caagcttgtt cgc                                            23

<210> SEQ ID NO 8
<211> LENGTH: 63
<212> TYPE: DNA
<213> ORGANISM: Artificial Sequence
<220> FEATURE:
<223> OTHER INFORMATION: PCR primer

<400> SEQUENCE: 8

```
ttctggatcc atggtgatcc tcctaagatc taagcttcaa ttgtttgatt ggatttttatt    60 ttg                                                                  63
```

```
<210> SEQ ID NO 9
<211> LENGTH: 34
<212> TYPE: DNA
<213> ORGANISM: Artificial Sequence
<220> FEATURE:
<223> OTHER INFORMATION: PCR primer

<400> SEQUENCE: 9
aaaagcatta agctttctgt atgatgaata aggg                                 34
```

```
<210> SEQ ID NO 10
<211> LENGTH: 32
<212> TYPE: DNA
<213> ORGANISM: Artificial Sequence
<220> FEATURE:
<223> OTHER INFORMATION: PCR primer

<400> SEQUENCE: 10
caacggatcc tttttcttct gacattgtgt tc                                   32
```

```
<210> SEQ ID NO 11
<211> LENGTH: 24
<212> TYPE: DNA
<213> ORGANISM: Artificial Sequence
<220> FEATURE:
<223> OTHER INFORMATION: PCR primer

<400> SEQUENCE: 11
aaacctgagc aagcagaagg cgca                                            24
```

```
<210> SEQ ID NO 12
<211> LENGTH: 26
<212> TYPE: DNA
<213> ORGANISM: Artificial Sequence
<220> FEATURE:
<223> OTHER INFORMATION: PCR primer

<400> SEQUENCE: 12
gcacttgtca caagtttaga ataacg                                          26
```

```
<210> SEQ ID NO 13
<211> LENGTH: 25
<212> TYPE: DNA
<213> ORGANISM: Artificial Sequence
<220> FEATURE:
<223> OTHER INFORMATION: PCR primer

<400> SEQUENCE: 13
ctactatttc aacacagcta tctgc                                           25
```

```
<210> SEQ ID NO 14
<211> LENGTH: 24
<212> TYPE: DNA
<213> ORGANISM: Artificial Sequence
<220> FEATURE:
<223> OTHER INFORMATION: PCR primer

<400> SEQUENCE: 14
ggagggttca aatcgaaaga aagc                                            24
```

```
<210> SEQ ID NO 15
<211> LENGTH: 55
```

```
<212> TYPE: DNA
<213> ORGANISM: Artificial Sequence
<220> FEATURE:
<223> OTHER INFORMATION: PCR primer

<400> SEQUENCE: 15
acatgtattc acgaacgaaa atcgacatga tctgcacctt ttttatcttt attcg      55

<210> SEQ ID NO 16
<211> LENGTH: 52
<212> TYPE: DNA
<213> ORGANISM: Artificial Sequence
<220> FEATURE:
<223> OTHER INFORMATION: PCR primer

<400> SEQUENCE: 16
attttagaaa acaataaacc cttgcaatgg cagaattacg cagtaatatg at         52

<210> SEQ ID NO 17
<211> LENGTH: 51
<212> TYPE: DNA
<213> ORGANISM: Artificial Sequence
<220> FEATURE:
<223> OTHER INFORMATION: PCR primer

<400> SEQUENCE: 17
ggactgatct ccaagcgatg gcatgatctg cacctttttt atctttattc g          51

<210> SEQ ID NO 18
<211> LENGTH: 50
<212> TYPE: DNA
<213> ORGANISM: Artificial Sequence
<220> FEATURE:
<223> OTHER INFORMATION: PCR primer

<400> SEQUENCE: 18
tcgagaatta aaggagggtt tcatatggca gaattacgca gtaatatgat            50

<210> SEQ ID NO 19
<211> LENGTH: 29
<212> TYPE: DNA
<213> ORGANISM: Artificial Sequence
<220> FEATURE:
<223> OTHER INFORMATION: PCR primer

<400> SEQUENCE: 19 attcttttc ttctgacatt gtgttcacc                                    29

<210> SEQ ID NO 20
<211> LENGTH: 20
<212> TYPE: DNA
<213> ORGANISM: Artificial Sequence
<220> FEATURE:
<223> OTHER INFORMATION: PCR primer

<400> SEQUENCE: 20
caatattaat agttggaggg                                             20

<210> SEQ ID NO 21
<211> LENGTH: 34
<212> TYPE: DNA
<213> ORGANISM: Artificial Sequence
<220> FEATURE:
<223> OTHER INFORMATION: PCR primer

<400> SEQUENCE: 21
```
aatgtcagaa gaaaaagaat ttaggaggat cacc                                       34

<210> SEQ ID NO 22
<211> LENGTH: 20
<212> TYPE: DNA
<213> ORGANISM: Artificial Sequence
<220> FEATURE:
<223> OTHER INFORMATION: PCR primer

<400> SEQUENCE: 22
ccctccaact attaatattg                                                       20

<210> SEQ ID NO 23
<211> LENGTH: 30
<212> TYPE: DNA
<213> ORGANISM: Artificial Sequence
<220> FEATURE:
<223> OTHER INFORMATION: PCR primer

<400> SEQUENCE: 23
ggggtatatc acgtctgcag attttcttgc                                            30

<210> SEQ ID NO 24
<211> LENGTH: 39
<212> TYPE: DNA
<213> ORGANISM: Artificial Sequence
<220> FEATURE:
<223> OTHER INFORMATION: PCR primer

<400> SEQUENCE: 24
ccctccaact atctagatat tgttacttac tataaatag                                  39

<210> SEQ ID NO 25
<211> LENGTH: 41
<212> TYPE: DNA
<213> ORGANISM: Artificial Sequence
<220> FEATURE:
<223> OTHER INFORMATION: PCR primer

<400> SEQUENCE: 25
ggcgtaatat gagttcaaca aaagacaaat gtcagcttca c                               41

<210> SEQ ID NO 26
<211> LENGTH: 47
<212> TYPE: DNA
<213> ORGANISM: Artificial Sequence
<220> FEATURE:
<223> OTHER INFORMATION: PCR primer

<400> SEQUENCE: 26
cctgtacatt agtccccatg ctagctcctc cttttggatt ttcatcc                         47

<210> SEQ ID NO 27
<211> LENGTH: 33
<212> TYPE: DNA
<213> ORGANISM: Artificial Sequence
<220> FEATURE:
<223> OTHER INFORMATION: PCR primer

<400> SEQUENCE: 27
ctttgaattc gcaagatatc attaatgtat gcc                                        33

<210> SEQ ID NO 28
<211> LENGTH: 23
<212> TYPE: DNA
<213> ORGANISM: Artificial Sequence

```
<220> FEATURE:
<223> OTHER INFORMATION: PCR primer

<400> SEQUENCE: 28
gcaagatatc attaatgtat gcc                                          23

<210> SEQ ID NO 29
<211> LENGTH: 35
<212> TYPE: DNA
<213> ORGANISM: Artificial Sequence
<220> FEATURE:
<223> OTHER INFORMATION: PCR primer

<400> SEQUENCE: 29
gacatagacg ccagtcccga tattattgcg gtagc                             35

<210> SEQ ID NO 30
<211> LENGTH: 59
<212> TYPE: DNA
<213> ORGANISM: Artificial Sequence
<220> FEATURE:
<223> OTHER INFORMATION: PCR primer

<400> SEQUENCE: 30
aattagctag ctcctccttt tggatccttt aaataagtga gagatattta tattgaggg   59

<210> SEQ ID NO 31
<211> LENGTH: 30
<212> TYPE: DNA
<213> ORGANISM: Artificial Sequence
<220> FEATURE:
<223> OTHER INFORMATION: PCR primer

<400> SEQUENCE: 31
agtaggatcc agagggagtg gttaacgggc                                   30

<210> SEQ ID NO 32
<211> LENGTH: 51
<212> TYPE: DNA
<213> ORGANISM: Artificial Sequence
<220> FEATURE:
<223> OTHER INFORMATION: PCR primer

<400> SEQUENCE: 32
tatgagataa tgccgactgt acttacgcgt cgccgctttg gacgcagtgt c           51

<210> SEQ ID NO 33
<211> LENGTH: 71
<212> TYPE: DNA
<213> ORGANISM: Artificial Sequence
<220> FEATURE:
<223> OTHER INFORMATION: PCR primer

<400> SEQUENCE: 33
ccacctgtac attagtcccc atatgagttt cacctcctta ctcgaggtac ccgaaaattg  60
gataaagtgg g                                                       71

<210> SEQ ID NO 34
<211> LENGTH: 51
<212> TYPE: DNA
<213> ORGANISM: Artificial Sequence
<220> FEATURE:
<223> OTHER INFORMATION: PCR primer

<400> SEQUENCE: 34
```
gacactgcgt ccaaagcggc gacgcgtaag tacagtcggc attatctcat a    51

<210> SEQ ID NO 35
<211> LENGTH: 71
<212> TYPE: DNA
<213> ORGANISM: Artificial Sequence
<220> FEATURE:
<223> OTHER INFORMATION: PCR primer

<400> SEQUENCE: 35
cccactttat ccaattttcg ggtacctcga gtaaggaggt gaaactcata tggggactaa    60
tgtacaggtg g    71

<210> SEQ ID NO 36
<211> LENGTH: 29
<212> TYPE: DNA
<213> ORGANISM: Artificial Sequence
<220> FEATURE:
<223> OTHER INFORMATION: PCR primer

<400> SEQUENCE: 36
tttgagctcg gtttaacacc ccggagcgg    29

<210> SEQ ID NO 37
<211> LENGTH: 32
<212> TYPE: DNA
<213> ORGANISM: Artificial Sequence
<220> FEATURE:
<223> OTHER INFORMATION: PCR primer

<400> SEQUENCE: 37
ctttacgcgt caagatatca ttaatgtatg cc    32

<210> SEQ ID NO 38
<211> LENGTH: 42
<212> TYPE: DNA
<213> ORGANISM: Artificial Sequence
<220> FEATURE:
<223> OTHER INFORMATION: PCR primer

<400> SEQUENCE: 38
ttttggtacc tttaaataag tgagagatat ttatattgag gg    42

<210> SEQ ID NO 39
<211> LENGTH: 33
<212> TYPE: DNA
<213> ORGANISM: Artificial Sequence
<220> FEATURE:
<223> OTHER INFORMATION: PCR primer

<400> SEQUENCE: 39
gggttacgcg tggccgctaa ctacactaac agc    33

<210> SEQ ID NO 40
<211> LENGTH: 31
<212> TYPE: DNA
<213> ORGANISM: Artificial Sequence
<220> FEATURE:
<223> OTHER INFORMATION: PCR primer

<400> SEQUENCE: 40
gggttggtac ctttaattct cgagtgttaa g    31

<210> SEQ ID NO 41
<211> LENGTH: 18

<210> SEQ ID NO 41
<211> LENGTH: 18
<212> TYPE: DNA
<213> ORGANISM: Artificial Sequence
<220> FEATURE:
<223> OTHER INFORMATION: PCR primer

<400> SEQUENCE: 41
tgtacacaga cgatgagc                                                       18

<210> SEQ ID NO 42
<211> LENGTH: 45
<212> TYPE: DNA
<213> ORGANISM: Artificial Sequence
<220> FEATURE:
<223> OTHER INFORMATION: PCR primer

<400> SEQUENCE: 42
ctaatacgac tcactatagg gagttagatt ctgaataacg ttctt               45

<210> SEQ ID NO 43
<211> LENGTH: 18
<212> TYPE: DNA
<213> ORGANISM: Artificial Sequence
<220> FEATURE:
<223> OTHER INFORMATION: PCR primer

<400> SEQUENCE: 43
agagaacgta ttggctgg                                                       18

<210> SEQ ID NO 44
<211> LENGTH: 45
<212> TYPE: DNA
<213> ORGANISM: Artificial Sequence
<220> FEATURE:
<223> OTHER INFORMATION: PCR primer

<400> SEQUENCE: 44
ctaatacgac tcactatagg gagccactac ttcgatttga tgttc               45

<210> SEQ ID NO 45
<211> LENGTH: 18
<212> TYPE: DNA
<213> ORGANISM: Artificial Sequence
<220> FEATURE:
<223> OTHER INFORMATION: PCR primer

<400> SEQUENCE: 45
ggttcttcct gtcgattc                                                       18

<210> SEQ ID NO 46
<211> LENGTH: 45
<212> TYPE: DNA
<213> ORGANISM: Artificial Sequence
<220> FEATURE:
<223> OTHER INFORMATION: PCR primer

<400> SEQUENCE: 46
ctaatacgac tcactatagg gaggctgatt ttcaaggtca acagt               45

<210> SEQ ID NO 47
<211> LENGTH: 277
<212> TYPE: DNA
<213> ORGANISM: Bacillus subtilis PA432

<400> SEQUENCE: 47
caacaaaaga caacagtccc gatattattg cggtagcggg cggatcatca aaagccgaag     60

-continued

```
cgatcgaggc ttactttaaa aagccacgca acacggttct cgtcacagac gaaggagccg    120
caaagaagtt attaagggat gaataatccc tcaatataaa tatctctcac ttatttaaag    180
gatccaaaag gaggagctag catggggact aatgtacagg atccccagct tgttgataca    240
ctaatgcttt tatataggga aaaggtggtg aactact                             277

<210> SEQ ID NO 48
<211> LENGTH: 34
<212> TYPE: DNA
<213> ORGANISM: Artificial Sequence
<220> FEATURE:
<223> OTHER INFORMATION: PCR primer

<400> SEQUENCE: 48
acaaagacaa cagtccggtt ctcgtcacag acga                                34

<210> SEQ ID NO 49
<211> LENGTH: 37
<212> TYPE: DNA
<213> ORGANISM: Artificial Sequence
<220> FEATURE:
<223> OTHER INFORMATION: PCR primer

<400> SEQUENCE: 49
cccatgctag ctcctccttt tggatccttt aaataag                             37
```

METHOD FOR MRNA STABILIZATION

This application is the U.S. national phase of International Application No. PCT/EP2006/011547, filed 1 Dec. 2006, which designated the U.S. and claims priority to Europe Application No. 05026475.3, filed 5 Dec. 2005; the entire contents of each of which are hereby incorporated by reference.

Pantothenate is a member of the B complex of vitamins and is a nutritional requirement for mammals including humans and livestock. In cells, pantothenate is converted to coenzyme A (CoA) and acyl carrier protein, the biologically active forms of the cofactor. These two coenzymes participate in over 100 different enzymatic reactions in the cell.

Published PTC patent applications WO 01/21772, WO 02/057474, WO 02/061108, and WO 04/005527 (all filed by Omnigene Bioproducts Inc., USA) describe methods to produce pantothenate using strains of *Bacillus subtilis* 168 that have higher expression levels of biosynthetic genes involved in pantothenate production. These genes include panB, panC, panD, panE, ilvB, ilvN, ilvC, ilvD, glyA, and serA. To achieve higher expression levels of these genes, the native promoters controlling transcription of said genes were removed and replaced by stronger constitutive promoters derived from an endogenous bacteriophage, SPO1, using standard genetic recombinant methods known in the art. Increasing the levels of transcription of a gene is well known in the art to lead to higher levels of the protein encoded by the overexpressed gene.

It is also well known in the art that overproduction of proteins by means of transcription overexpression may lead to undesirable effects on cellular metabolism (WO 98/07846). Furthermore, it has also been described that protein overproduction may lead to deleterious effects in the translational machinery of the host cell (Hengjiang et al., 1995, *J. Bacteriol.* 177:1497-1504) and/or induction of proteolytic activities mediated by stress responses (Ramirez D. M., and W. E. Bentley, 1995, *Biotechnol. Bioeng.* 47:596-608) which could be the consequence of lower production titers. Therefore, devising methods for protein overproduction alternative to the use of constitutive strong promoters could be advantageous for the production at industrial scale of fine chemicals, like such as pantothenate.

Transcript degradation is utilized by microorganisms as a means to control cellular protein content. On the other hand, microorganisms have developed mechanisms by which the stability of a given transcript is enhanced. To achieve this, transcripts are provided with nucleotide sequences capable of forming secondary structures which impose an impediment for mRNA degrading enzymes to exert their action. Despite substantial knowledge about mRNA degradation and stability, there are only a few examples where this knowledge has been applied for the expressed purpose of redirecting bacterial carbon flow for the production of fine chemicals.

Smolke et al. (2001, *Metabolic Engineering.* 3: 313-321) describe the use of artificially generated sequences capable of stem-loop structure formation as mRNA stability elements to increase the steady-state level of transcripts encoded by two plasmid-borne crt genes in order to increase phytoene production in *Escherichia coli*. For this method to be useful, the above-mentioned mRNA stability elements must be precisely placed no more than one nucleotide away from a promoter transcriptional start site (Carrier and Keasling 1999, *Biotechnol. Prob.* 15: 58-64). Alternatively, if cleavage is desired at a site within the native mRNA molecules, the mRNA stabilizing element is required to be co-introduced with an RNase E cleavage site so that RNase E—specific cleavage results in a new mRNA molecule of similar structure, i.e. placement of the RNA stability element one (1) nucleotide from the 5' end. Either example requires laborious experimental work, limiting the usefulness of the method. Thus the development of stabilizing mRNA independent of promoters transcriptional start sites or independent of RNase E cleavage could offer a better alternative to engineer microorganisms interesting for the manufacture of fine chemicals and/or proteins at the industrial level.

Gene orthologs to *E. coli* RNase E have not been found in microorganisms interesting for the manufacture of metabolites and/or proteins at industrial scale (Condon, 2003, *Microbiol. Mol. Biol. Rev.* 67:157-174). For *Bacillus subtilis*, evidence suggests that this bacterium contains two genes (ykqC [RNAseJ1] and ymfA [RNAseJ2]) which could be functionally homologous to *E. coli* RNase E, yet do not show any significant nucleotide or amino acid sequence similarity (Even et al., 2005, *Nucleic Acids Res.* 33:2141-2152). Accordingly, the transcript degradation machinery of *B. subtilis* is quite different: only 6 out of 17 characterized *E. coli*-like enzymes involved in RNA degradation activities have been identified in *B. subtilis*.

The above cited mRNA stabilization methods were first applied to plasmid-based replicons containing only one gene. Widner et al. (1999, WO99/43835) discloses a method for producing a polypeptide in *B. subtilis* by addition of a stabilizing element from the *B. thuringiensis* cryIIIA gene inserted between tandem promoters and the structural gene encoding the polypeptide. However the presence of two promoters was necessary to achieve "saturating levels of mRNA" (WO99/43835). Hue et al. (1995, *J. Bacteriol.* 177:3465-3471) discloses a 5' mRNA stabilizer which stabilizes mRNA sequences by homology to the 3' end of 16S RNA. Also, Daguer et al. (2005, *Lett. Appl. Microbiol.* 41:221-226) discloses a plasmid-based mRNA stabilization method in which ribosomes bind to ribosome binding sites to generate RNA stability. This method achieved only a rather insignificant increase in product formation (i.e. 1.5 fold increase in levansucrase production), and in some cases actually decrease formation of a protein product.

Moreover, biosynthesis of fine chemicals, proteins, and other chemical compounds often utilize complex multi-gene clusters (i.e. operons) located at different sites on the chromosome and which generate multiple mRNA transcripts. Consequently, such previous cited mRNA stabilization methods could be ill-suited to increase the protein synthesis since expression of cloned multi-gene clusters from plasmids can sometimes be unstable (Kim et al., 1982, Han'guk Saenghwa Hakhoechi 15:305-314; Gryczan, 1982, The Molecular Biology of the Bacilli [Dubnau, ed.], Academic Press, New York, N.Y., pp 307-329; Piece and Gutteridge, 1985, App. Environ. Microbiol. 49:1094-1100; Newell et al., 1987, Biochem. Soc. Trans. 15:281-282; Haeseleer, 1994, Res. Microbiol. 145:683-387; Al-Allaf et al., 2005, J. Biochem. Biophys. Methods 64:142-146). Notwithstanding, patent application WO 02/055711 discloses the possibility of improving the expression of genes involved in pantothenate production of *Corynebacterium glutamicum* (viz. at least one of ilvBN, ilvC, ilvD, panB, panC, and panD) by prolonging the lifetime of their mRNA transcripts, however, without disclosing how this can be achieved.

Consequently, it is an object of the present invention to provide a method to increase the production of a desired chemical compound in a microorganism without strengthening native promoter signals controlling transcription of said structural gene sequences, viz. by the introduction of a DNA sequence at the 5' end of the encoding DNA gene sequence capable of forming a stem loop and capable of increasing the stability of mRNA transcripts from one or more genes. This method is characterized in that the loop-forming DNA sequence is introduced seven or more DNA unpaired nucleotides down-stream of the start site of transcription of the relevant gene(s) of the microorganism.

It is a further object of the present invention to provide stabilized mRNA sequences which contain a stabilizing element at their 5' end. The stabilizing element is transcribed from a DNA sequence introduced seven or more DNA unpaired nucleotides down-stream of the start of transcription of the relevant gene of the microorganism. Addition of this stabilizing element has the effect that the mRNA is no longer or less accessible to enzymatic degradation and thus a higher production of a desired chemical compound in a microorganism is the result.

In a further embodiment the present invention relates to corresponding DNA sequences containing these mRNA stabilizing sequences and which upon transcription by a microorganism result stabilized mRNA transcripts, as well as to transformed microorganisms comprising such DNA sequences.

Finally, the use of such DNAs or stabilized mRNA transcripts in a method to increase the stability of mRNA transcripts of one or more genes that generate multiple mRNA transcripts and that are located on a chromosome, plasmid or any other self-replicating DNA molecule, or a method to increase the production of a desired chemical compound by a transformed microorganism, respectively, are objects of the present invention.

The term "chemical compound" means any carbon-based substance originating from cellular metabolism, i.e. the breakage and/or formation of one or more chemical bonds in a reaction facilitated by one or more enzymes in a cell that has biological activity. Examples of such compounds are proteins, enzymes, nucleotides, ribonucleotides, amino acids, vitamins (e.g. ascorbic acid, pantothenic acid), vitamin-like substances (e.g. coenzyme Q10), carotenoids, lipids and fatty acids.

The term "microorganism" means a microscopic, self-reproducing, respiring organism including, but not limited to, bacteria, fungi (including yeast) and algae. The term bacteria includes both Gram-negative and Gram-positive microorganisms. Examples of Gram negative bacteria are any from the genera *Escherichia*, *Gluconobacter*, *Rhodobacter*, *Pseudomonas*, and *Paracoccus*. Gram-positive bacteria are selected from, but not limited to any of the families Bacillaceae, Brevibacteriaceae, Corynebacteriaceae, Lactobacillaceae, and Streptococaceae and belong especially to the genera *Bacillus*, *Brevibacterium*, *Corynebacterium*, *Lactobacillus*, *Lactococcus* and *Streptomyces*. Among the genus *Bacillus*, *B. subtilis*, *B. amyloliquefaciens*, *B. licheniformis* and *B. pumilus* are preferred microorganisms in the context of the present invention. Among *Gluconobacter*, *Rhodobacter* and *Paracoccus*, *G. oxydans*, *R. sphaeroides* and *P. zeaxanthinifaciens* are preferred, respectively. Examples of yeasts are *Saccharomyces*, particularly *S. cerevisiae*. Examples of preferred other fungi are *Aspergillus niger* and *Pencillium chrysogenum*.

The phrase "strengthening of native promoter signals" refers to any genetic change of one or more nucleotides within a contiguous DNA sequence that interacts with RNA polymerase (for example, but not limited to, the "−35" and "−10" binding sites), which results in the synthesis of a greater number of messenger RNA molecules (i.e. RNA transcripts) compared to the unmodified DNA sequence. The phrase also comprises replacement of a promoter by a stronger one.

Methods of strengthening native promoter signals are well-known and generally used in the art. The phrase "without strengthening native promoter signals" is used to indicate that the method of increasing the production of a desired chemical compound in a microorganism in accordance with the present invention is different from these well-known methods. This phrase, however, does not mean that methods which combine the present new method and the well-known methods are not encompassed by the present invention.

The term "promoter signals" means a contiguous DNA nucleotide sequence that specifically interacts with RNA polymerase (for example, but not limited to, the "−35" and "−10" binding sites), and allows for initiation of messenger RNA synthesis (i.e. synthesis of RNA transcripts).

The term "native promoter signal" means a naturally occurring promoter signal found in a microorganism.

The phrase "introduction of a DNA sequence" refers to any addition or insertion of a DNA sequence by DNA transformation, conjugation or transduction into the chromosome of a microorganism. Said addition or insertion occurs by DNA recombination that may or may not also result in a removal or deletion of chromosomal DNA nucleotides. Methods by which introduction of DNA sequences into microorganisms are achieved, especially by site-specific introduction, are well-known in the art and described in text books and scientific literature. They are standard procedures practiced by persons skilled in the art. The DNA sequence capable of forming one or more stem loops is introduced seven or more unpaired DNA nucleotides, i.e. at least 7, e.g. 8, 9, 10 or 11 down-stream of the start site of transcription of the relevant gene(s) of the microorganism. The number and kind of nucleotide changes are limited by the fact that no sequence is formed representing an RNase E-specific nuclease cleaving site.

The term "increasing the stability of mRNA" means extending the half-life of mRNA sequences or blocking/delaying their degradation.

The DNA sequence to be introduced (i.e. mRNA stabilizing element) can be any sequence capable of forming a double-stranded stem loop, viz. a sequence which is naturally occurring or derived from a naturally occurring sequence or a sequence which is completely or partly synthesized using methods well-known in the art. The sequence can be of any length but preferably consists of a minimum of 15 nucleotides, more preferably 23-100 nucleotides. The stem should consist of at least 6 base pairs, preferably at least 10 base pairs (with mismatch nucleotides or bulge loops possibly being present) and the loops may consist of 3-30 nucleotides. The calculated thermodynamic stability (AG) of the stem loop should be −2.8 kcal/mol or lower, preferably −5 kcal/mol or lower, according to algorithms developed by Zuker (2003, Nucleic Acids Res. 31:3406-3415), preferably lower, i.e. −3, −4, −5 or −6, preferably lower than −7, e.g. −8, −9, −10, −11 or −12 kcal/mol. In a preferred embodiment of the invention the DNA sequence to be introduced is a genome sequence or sequence derived from the genome of a microorganism, i.e. the same or a different microorganism to be used for the production of the desired chemical compound. In a particular/preferred embodiment of the present invention the DNA sequence is derived from the genome of a *Bacillus*, especially from *B. subtilis*. Examples of such sequences are contiguous sequences occurring in sequences from gene cggR to gene gapA, from gene hrcA to gene grpE, from gene ilvN to gene ilvC, from gene aprE to gene yhfO, from gene ybdA to gene gsiB and from gene ytxC to gene thrS of *B. subtilis* and particularly those represented by SEQ ID Nos. 1-6. The term "sequence occurring in a sequence from gene . . . to gene . . .

" means a sequence between these two genes, i.e. the whole sequence or part thereof, including sequences extending to the genes themselves.

Generally, a nucleic acid is considered to be within the scope of this invention if it is at least 70%, preferably at least 80%, or most preferably at least 90%, homologous to a naturally occurring nucleic acid sequence that can generate a mRNA stabilizing element. Such homology can be determined experimentally by Southern hybridization analysis under the following conditions: hybridization in 5×SSC, 10-50% formamide, 1×Denhardts solution, 100 µg/ml denatured salmon sperm DNA at 37-42° C.

SEQ ID No. 1 represents the cggR-gapA gene sequence.
SEQ ID No. 2 represents a specific sequence between the genes cggR and gapA.
SEQ ID No. 3 represents the hrcA-grpE gene sequence.
SEQ ID No. 4 represents a specific sequence between the genes hrcA and grpE
SEQ ID No. 5 represents a chromosomal DNA sequence in which a cggR-gapA stabilizing element is inserted within the 5' leader sequence of the ilvB gene in the operon ilvBNC.
SEQ ID No. 6 represents a chromosomal DNA sequence in which a hrcA-grpE stabilizing element is inserted within the 5' leader sequence of the ilvD gene.

While the method of the present invention will be described in detail with respect to the expression of pantothenic acid one skilled in the art will recognize that this method can be applied universally to increase the production of any microbial metabolite or of any chemical compound and/or protein to be synthesized by microbial cells that utilize gene-encoded biosynthetic enzymes that convert a substrate (e.g. glucose) or precursor (e.g. pyruvate) to such a chemical compound or to increase the production of any protein.

EXAMPLES

General Methodology

Strains and plasmids. *Bacillus subtilis* strains of the present invention are derived from strains CU550 (trpC2 ilvC leuC) and 1A747 (SPβ$^c$, prototroph), which are derivatives of *B. subtilis* 168 (trpC2). Both strains were obtained from the *Bacillus* Genetic Stock Center, The Ohio State University, Columbus, Ohio 43210 USA. *E. coli* strain Top10 (Invitrogen) was utilized for regular cloning purposes. Plasmids pUC18, pUC19, and pBR322 (New England Biolabs) were used as general purpose cloning vectors. Antibiotic resistance genes that confer resistance to chloramphenicol (cat), tetracycline (tet), erythromycin (erm), and spectinomycin (spec) were obtained from plasmid pC194 (GeneBank M19465, Cat#1E17 *Bacillus* Genetic Stock Center, The Ohio State University, Columbus, Ohio 43210 USA), pBC16 (GeneBank X51366, Cat#1E9 *Bacillus* Genetic Stock Center), pDG646 and pDG1726 (Guérot-Fleury et. al., 1995, *Gene* 167:335-336). The $P_{26}$ and $P_{15}$ promoters of the *B. subtilis* bacteriophage SPO1 (Lee et al., 1980, *Mol. Gen. Genet.* 180:57-65) was obtained from plasmids pUC18SP01-26 and pXI23roDTD-SPO1-15, a derivative of plasmid pX12 (Hümbelin et al., 1999, *J. Ind. Microbiol. Biotech.* 22:1-7), respectively.

Media. Standard minimal medium (MM) for *B. subtilis* contains 1× Spizizen salts, 0.04% sodium glutamate, and 0.5% glucose. Standard solid complete medium is Tryptose Blood Agar Broth (TBAB, Difco). Standard liquid complete medium is Veal Infusion-Yeast Extract broth (VY). The compositions of these media are described below:

TBAB medium: 33 g Difco Tryptose Blood Agar Base (Catalog #0232), 1 L water. Autoclave.

VY medium: 25 g Difco Veal Infusion Broth (Catalog #0344), 5 g Difco Yeast Extract (Catalog #0127), 1 L water. Autoclave.

Minimal Medium (MM): 100 ml 10× Spizizen salts; 10 ml 50% glucose; 1 ml 40% sodium glutamate, qsp 1 L water.

10× Spizizen salts: 140 g $K_2HPO_4$; 20 g $(NH_4)_2SO_4$; 60 g $KH_2PO_4$; 10 g $Na_3$ citrate.$2H_2O$; 2 g $MgSO_4.7H_2O$; qsp 1 L with water.

VFB MMGT medium: 100 ml 10×VFB MM; 100 ml 0.5 M Tris (pH 6.8); 44 ml 50% glucose; 2 ml Trace elements solution; 2 ml Fe solution; 2 ml $CaCl_2$ solution; 2 ml Mg/Zn solution; 748 ml sterile distilled water.

10×VFB minimal medium (10× VFB MM): 2.5 g Na-glutamate; 15.7 g $KH_2PO_4$; 15.7 g $K_2HPO_4$; 27.4 g $Na_2HPO_4.12H_2O$; 40 g $NH_4Cl$; 1 g citric acid; 68 g $(NH_4)_2SO_4$; qsp 1 L water.

Trace elements solution: 1.4 g $MnSO_4.H_2O$; 0.4 g $CoCl_2.6H_2O$; 0.15 g $(NH_4)_6Mo_7O_{24}.4H_2O$; 0.1 g $AlCl_3.6H_2O$; 0.075 g $CuCl_2.2H_2O$; qsp 200 ml water.

Fe solution: 0.21 g $FeSO_4.7H_2O$; qsp 10 ml water.

$CaCl_2$ solution: 15.6 g $CaCl_2.2H_2O$; qsp 500 ml water.

Mg/Zn solution: 100 g $MgSO_4.7H_2O$; 0.4 g $ZnSO_4.7H_2O$; qsp 200 ml water.

SMG medium: 62.78 g MOPS, 20 g Cargill soy four (200/20), 1 ml PSTE-1000× solution, 5 g Na-glutamate and 8 g $(NH_4)_2SO_4$, water up to 735 ml (pH 7.2); autoclaved (30 min. at 121° C.). After autoclaving, 100 ml 1 M K-phosphate buffer (pH 7.2), 120 ml 50% glucose, 10 ml 1 M $MgSO_4.7H_2O$, 1.4 ml 1 M $CaCl_2.2H_2O$ and 35 ml sterile distilled water was added.

PSTE-1000× solution: 0.2 g $MnCl.4H_2O$; 0.15 g $ZnSO_4.7H_2O$; 0.2 g $CoCl_2.6H_2O$; 0.025 g $CuSO_4.5H_2O$; $Na_2MoO_4.2H_2O$; qsp 100 ml water.

Antibiotics: Ampicillin (Amp) or kanamycin (Km) were utilized at concentrations of 100 µg/ml and 50 µg/ml, respectively, to transform and propagate plasmids in *E. coli* cells grown in LB complex medium. To transform antibiotic gene-containing DNA fragments into *B. subtilis*, 5 µg/ml chloramphenicol (Cm), 15 µg/ml tetracycline (Tc) and 50 µg/ml spectinomycin (Spec) was added to the media. For erythromycin (Erm).gene selection, a mixture of 1 µg/ml erythromycin/25 µg/ml lincomycin was used.

Pantothenate Assays in Shake Flasks:

Shake flask culture conditions: Cell cultures grown overnight in VY rich medium were used to inoculate VFB MMGT medium (1:100 dilution). Growth was monitored until cells reached an $OD_{600}$ of ~0.6-0.8 at which time they were diluted once more in same medium to an $OD_{600}$ of 0.03. Growth was resumed for an additional 18 hours after which samples were collected, cells removed and supernatant analyzed by HPLC. Alternatively cell cultures grown overnight can be used to inoculate SMG medium and supernatants analyzed by HPLC after 24 hours growth.

HPLC assay: Chromatography of samples was performed on a Phenomenex LUNA C8 column, using an Agilent 1100 HPLC system equipped with a thermostat-maintained autosampler and a diode array detector. The column dimensions are 150×4.6 mm, particle size 5 micron. The column temperature was kept constant at 20° C. The mobile phase is a mixture of 0.1% acetic acid (A) and methanol (B). Gradient elution is applied, ranging from 1% B to 45% B in 15 minutes. The flow rate is 1 ml/min. Pantothenate was monitored using UV absorption at 220 nm, and is eluted at approximately 9.6 min. The calibration range of the method is from 1 to 100 mg/l pantothenate.

Molecular and genetic techniques. Standard genetic and molecular biology techniques are generally know in the art and have been previously described. DNA transformation, PBS1 generalized transduction, and other standard *B. subtilis* genetic techniques are also generally know in the art and have been described previously (Harwood and Cutting (eds), 1992, Molecular biological methods for *Bacillus*. New York: John Wiley and Sons).

Northern blot analysis. Cells grown in VFB MMGT medium on the logarithmic phase ($OD_{600}=\sim0.6$) were harvested at 4° C. and immediately frozen in liquid nitrogen after decanting of supernatant. Total RNA was extracted as follows. The pellet was resuspended in ice-cold TE buffer (10 mM Tris, 1 mM EDTA, pH 8.0). The cells were lysed in a mixture containing macaloid, phenol/chloroform, SDS and acid-washed glass beads by shaking in a bead beater (BioSpec) for 2 min. After centrifugation the supernatant was subjected to phenol/chloroform extraction three times. Total RNA was resuspended in diethylpyrocarbonate (DEPC)-treated $H_2O$ after two steps of precipitation and washing. After DNase I treatment total RNA was purified using the RNeasy Midi Kit (Qiagen). In this step smaller RNA molecules like tRNAs were eliminated. For quality control an aliquot of total RNA was subjected to 1.2% agarose gel analysis and/or was analyzed on a RNA6000 NanoChip (Agilent BioAnalyzer). Equal amounts of total RNA were loaded on a 1.2% agarose gel and transcripts separated by electrophoresis. After transferring the RNAs from the agarose gels to nylon membranes, these were probed against DIG-labeled anti-sense mRNA probes. The probes were generated from PCR fragments including appropriate T7 polymerase binding sites by the use of primer pairs. Probe generation from these PCR fragments as well as blotted membrane testing was developed by the use of the DIG Northern Starter Kit (Roche Diagnostics) following manufacturer's instructions.

Example I

Introduction of mRNA Stabilizing Elements Downstream of the Native Promoter of *B. subtilis* ilvD Resulting in Increased Protein Synthesis To analyze the possibility of protein overproduction mediated by an unmodified promoter expressing a gene to be translated from a stabilized transcript, an mRNA stabilizing element was inserted as 5' untranslated leader region between the native ilvD promoter and the ilvD gene. PCR was used to generate a DNA fragment, which included the intergenic region existing between the *B. subtilis* genes ypgR and ilvD. This fragment, of 519 bp, was engineered to include BglII and HindIII contiguous restriction sites 21 bp upstream of ilvD translational start codon. Primers PilvD+7 and PilvD–2 (Table 1) were utilized to amplify a fragment from *B. subtilis* DNA, which spans the entire ypgR-ilvD intergenic region starting 250 bp from the ilvD translational start codon. The DNA fragment was cloned in pCRXLTOPO (Invitrogen), its identity confirmed by sequencing analysis, and isolated from the vector backbone as EcoRI/BamHI cassette. After ligation with likewise digested plasmid pDG1728 (Guerout-Fleury et al., 1996, Gene 180:57-61), the resulting pPA475 plasmid was transformed in *B. subtilis* 1A747 resulting in strain PA494, which contained a single copy of the ilvD promoter region transcriptionally fused to a lacZ gene integrated within the amyE gene, including BglII and HindIII sites upstream of the putative RBS of ilvD. A second promoter probe was generated to further analyze the effect on protein production by the introduction of an mRNA stabilizing element as untranslated leader sequence. Thus, a DNA fragment containing the hrcA-grpE intergenic region was amplified from *B. subtilis* chromosomal DNA by PCR using primers 2HrcLoop+ and 2HrcLoop– (Table 1). The synthesized fragment 127 bp was digested with BglII and HindIII and ligated to BglII/HindIII digested pPA475 DNA. The resulting plasmid pPA477 was then transformed in 1A747, selecting for spectinomycin resistance. This yielded strain PA517. Strains PA494 and PA517 are isogenic strains except PA494 contains an ilvD-lacZ fusion with the wild-type 5' untranslated leader region and PA517 contains an ilvD-lacZ fusion a 5' untranslated leader region with the hrcA-grpE RNA stabilizing element. In standard ONPG assays well known to those skilled in the art, strain PA517 produced four-fold more β-galactosidase activity than strain PA494 after 48 hours of growth in minimal medium shake flask cultures. This increase in β-galactosidase activity can only be attributed to the presence of the hrcA-grpE stabilizing element preceding the ilvD structural gene.

TABLE 1

List of primers used to engineer microorganisms overproducing the LacZ protein under control of naturally occurring and not modified promoters.

| Primer | ID No. | Sequence |
|---|---|---|
| PilvD + 7 | 7 | 5'-GCGACTCCAGCAAGCTTGTTCGC-3' |
| PilvD – 2 | 8 | 5'-TTCTGGATCCATGGTGATCCTCCTAAGATCT AAGCTTCAATTGTTTGATTGGATTTTATT TTG-3' |
| 2HrcLoop+ | 9 | 5'-AAAAGCATTAAGCTTTCTGTATGATGAATAA GGG-3' |
| 2HrcLoop– | 10 | 5'-CAACGGATCCTTTTTCTTCTGACATTGTG TTC-3' |

Example II

High Titers of Pantothenate Production can be Achieved when IlvD Protein is Overproduced Using Either a Constitutively-Expressed Exogenous Promoter or a Native Promoter Containing an mRNA Stabilizing Element To compare the effect on metabolite production of enzyme overexpression mediated by stabilization of mRNA expressed under the control of a native promoter with the method well described in prior art of substituting native promoters for constitutively expressed strong ones, two strains were obtained by engineering the chromosomal DNA regions upstream of the *B. subtilis* ilvD gene. A first strain was constructed to overexpress the IlvD protein under the control of the strong constitutive SP01-26 promoter. To do so, *B. subtilis* PA49 ($P_{15}$ panBCD $P_{15}$ panE) a derivative of strain CU550 that contains SP01-15 promoter modifications of pantothenate biosynthetic genes panBCD and panE (WO 2004/113510), was further modified to contain an ilvD gene the expression of which is controlled by the SP01-26 promoter. To achieve this, the promoter region of ilvD ($ilvD_p$) was first deleted from strain *B. subtilis* 1A747 by the use of Long Flanking Homology PCR (LFH-PCR). PCR-generated fragments F1 and F2 were obtained using primer pairs P1/ilvD/for, P2/ilvD/r/sp and P3/ilvD/f/sp, P4/ilvD/rev (Table 2), and *B. subtilis* 1A747 chromosomal DNA as template. These fragments were then used as primers in a second PCR reaction using as template the spectinomycin-resistance gene cassette from plasmid pSPEC12flip (Wade et al., 1999, J. Bacteriol. 181:4365-4373). This final PCR DNA product was transformed into *B. subtilis* 1A747 selecting for spectinomycin-resistance (Spec$^r$). Many Spec$^r$ colonies were recovered and several were confirmed to have a deletion of the ilvD promoter region by PCR analysis using primers P1ilvD/for and P4ilvD/rev. A 4000 bp PCR fragment (indication deletion of the ilvD promoter region) was detected using DNA isolated from Spec$^r$ colonies whereas DNA from non-transformed cells (no deletion) generated a 3000 bp fragment. Colonies were also tested for the expected auxotrophy to isoleucine (Ile), leucine (Leu), and valine (Val) amino acids: all Spec$^r$, PCR positive colonies failed to grow on minimal medium lacking Ile, Leu, and Val amino acids. One Spec$^r$, PCR positive, Ilv$^-$ auxotroph was named PA24 ($P_{15}$ panBCD $P_{15}$ panE $\Delta ilvD_p$::spec) and saved for further use. PA49 was next transduced with a PBS1 lysate of PA24, selecting for spectinomycin resistance (Spec). Spec$^r$ colonies were recovered and one was confirmed by PCR and Ilv auxotroph to contain the $\Delta ilvD_p$::spec mutation. This colony was renamed PA60 ($P_{15}$panBCD $P_{15}$panE $\Delta ilvD_p$::spec).

Strain PA24 was then used to generate an ilvD gene under the expression of the SP01-26 promoter. Two DNA fragments, F1 and F2, were generated by LFH-PCR using primer pairs P1/ilvD/for and P2/ilvD/f/26, and P3/ilvD/r/26 and P4/ilvD/rev, respectively (Table 2), and *B. subtilis* 1A747 chromosomal DNA as template. These fragments were then used in a second PCR reaction using as template the SP01-26-containing plasmid pUC18SP01-26. This final PCR DNA product was transformed into PA24 selecting for Ilv$^+$ prototrophy. Many Ilv$^+$ colonies were recovered and shown to have lost resistance of spectinomycin resistance (i.e., Spec$^s$) as expected by replacement of the spec gene with the $P_{26}$ promoter fragment. Moreover, diagnostic PCR analysis of several Ilv$^+$ Spec$^s$ colonies using primers P26-seq and P4ilvD/rev confirmed the presence of the $P_{26}$ promoter adjacent to the ilvD structural gene: a 2000 bp PCR fragment (indication of the presence of $P_{26}$) was detected using DNA isolated from Ilv$^+$ Specs colonies whereas DNA from non-transformed cells (no SP01-26 promoter) generated no PCR fragment with the same primers. DNA from non-transformed cells generated a 2000 bp PCR fragment (indication of the presence of $P_{wt}$) with primers ilvDwt-prom and P4ilvD/rev, whereas DNA from Ilv$^+$ Spec$^s$ colonies generated no PCR products. One Ilv$^+$ Specs PCR positive colony was renamed PA27 ($P_{26}$ ilvD). The $P_{26}$ ilvD modified gene was then transferred to *B. subtilis* PA60 ($P_{15}$ panBCD $P_{15}$ panE $\Delta ilvD_p$::spec) by PBS1 transduction using methods know by those skilled in the art. By selecting for Ilv$^+$ prototrophy and screening form Spec$^s$ colonies, the $\Delta ilvD_p$::spec was replaced by $P_{26}$ ilvD resulting in the strain PA62 ($P_{15}$ panBCD $P_{15}$ panE $P_{26}$ ilvD). DNA sequencing of the chromosomal $P_{26}$ ilvD region of PA62 detected a single point mutation within the ilvD coding region, which caused a Gly-to-Asp amino acid change in residue 320. The ilvD coding sequence was then restored to wild-type by first removing an internal segment of the ilvD gene encompassing this mutation, creating an auxotrophic IlvD$^-$ mutant of PA62 (renamed PA64), then by converting PA64 to Ilv$^+$ prototrophy using wild type chromosomal DNA, using methods well-known to the skilled worker in the field. This generated strain PA73 ($P_{15}$ panBCD $P_{15}$ panE $P_{26}$ ilvD).

A second strain isogenic to PA73 but containing an unmodified ilvD gene promoter region and an mRNA stabilizing element between the ilvD gene and its native promoter instead of a strong constitutive one was constructed as follows. Three overlapping DNA fragments of 272 bp, fragment F1, 1683 bp, fragment F2 and 1102 bp, fragment F3 respectively were generated by PCR. Fragment F1 was obtained by using plasmid pPA477 as template and the synthetic oligonucleotides PilvDHrcLoop- and PilvDUP+ (Table 2) as primers. Fragment F2 was obtained by using *B. subtilis* 168 chromosomal DNA as template and synthetic oligonucleotides P4/ilvD/rev and HrcALoopPilvD+ as primers (Table 2). Fragment F3 was obtained by the use of *B. subtilis* 168 as template and synthetic oligonucleotides PilvDUP- and P1/ilvD/for as primers (Table 2). Fragments F1 and F3 were purified by agarose gel, mixed, and used as template in yet a fourth PCR reaction which included oligonucleotides PilvDHrcLoop- and P'1ilvD as primers. This generated fragment F13 of 1354 bp. Fragment 2 was gel purified, mixed with fragment F1 and the mixture utilized as template in a fifth reaction which included oligonucleotides PilvDUP+ and P'4ilvD as primers. This generated fragment F12 of 1935 bp. Fragments F12 and F13 were cloned in pCRXLTOPO (invitrogen) following manufacturer instructions. This generated plasmids pF12 (Fragment F12 cloned in pCRXLTOPO) and pF13 (fragment F13 cloned in pCRXLTOPO). Fragment F13 was amplified again using pF13 as template and oligonucleotides PilvDHcr13+ and PilvDHcr13- as primers. This generated fragment F13_2. Fragment F13_2 was digested with PstI and XbaI and ligated to a likewise digested pUC19 plasmid (New England Biolabs). This yielded plasmid pUCPilvDHcr13. After digestion with KpnI and XbaI, fragment F12 was ligated to likewise digested plasmid pUCPilvDHcr13. The ligation mixture was directly transformed into PA60 competent cells obtaining this way strain PA590. Shake flask analysis in SMG medium revealed production titers of 1.7 g/l for PA49, 2.5 g/l for PA73 and 2.6 g/l for PA590, proving the ability of the engineered strain with the stabilized transcript to yield similar titers to that engineered with a constitutively expressed strong promoter.

TABLE 2

List of primers used to engineer the ilvD gene in pantothenate overproducer strains.

| Primer | ID No. | Sequence |
| --- | --- | --- |
| P1ilvD/for | 11 | 5'-AAACCTGAGCAAGCAGAAGGCGCA-3' |
| P4/ilvD/rev | 12 | 5'-GCACTTGTCACAAGTTTAGAATAACG-3' |
| P26-seq | 13 | 5'-CTACTATTTCAACACAGCTATCTGC-3' |
| ilvDwt-prom | 14 | 5'-GGAGGGTTCAAATCGAAAGAAAGC-3' |
| P2/ilvD/r/sp | 15 | 5'-ACATGTATTCACGAACGAAAATCGACATGATCTGCACCTTTTTTATCTTTATTCG-3' |
| P3/ilvD/f/sp | 16 | 5'-ATTTTAGAAAACAATAAACCCTTGCAATGGCAGAATTACGCAGTAATATGAT-3' |
| P2/ilvD/f/26 | 17 | 5'-GGACTGATCTCCAAGCGATGGCATGATCTGCACCTTTTTTATCTTTATTCG-3' |
| P3/ilvD/r/26 | 18 | 5'-TCGAGAATTAAAGGAGGGTTTCATATGGCAGAATTACGCAGTAATATGAT-3' |
| PilvDHrcLoop- | 19 | 5'-ATTCTTTTTCTTCTGACATTGTGTTCACC-3' |
| PilvDUP+ | 20 | 5'-CAATATTAATAGTTGGAGGG-3' |

TABLE 2-continued

List of primers used to engineer the ilvD
gene in pantothenate overproducer strains.

| Primer | ID No. | Sequence |
|---|---|---|
| HrcALoopPilvD+ | 21 | 5'-AATGTCAGAAGAAAAAGAATTTAGGA GGATCACC-3' |
| PilvDUP- | 22 | 5'-CCCTCCAACTATTAATATTG-3' |
| PilvDHcr13+ | 23 | 5'-GGGGTATATCACGTCTGCAGATTTTC TTGC-3' |
| PilvDHcr13- | 24 | 5'-CCCTCCAACTATCTAGATATTGTTAC TTACTATAAATAG-3' |

Example III

Introduction of mRNA Stabilizing Elements Downstream of the Native Promoter of the ilv Operon Increases Synthesis of Proteins The ability of an mRNA stabilizing element to induce protein overproduction was tested under the environment of another native promoter expressing genes involved in pantothenate synthesis. To do so, the promoter region of ilvB (ilvB$_p$) including the untranslated leader region was engineered to include two restriction sites to allow subsequent modification. The two restriction sites were located 474 bp (PshAI) and 7 bp (NheI) upstream of the ilvB structural gene translational start codon. Two overlapping PCR fragments were generated from B. subtilis 168 chromosomal DNA with primer pairs PilvUP2+, PilvUP- and Pilv+, Pilv- (Table 3). After assembling by a third PCR reaction to generate a single DNA fragment using the two shorter overlapping fragments as primers, the resulting fragment was TA-cloned in pCRX-LTOPO (Invitrogen) following manufacturer instructions, and its sequence confirmed. The cloned fragment was then removed by EcoRI/BamHI digestion and subcloned into the lacZ promoter probe vector pDG1728 (Guerout-Fleury et al., 1996, Gene 180:57-61) following procedures known to those skilled in the art, yielding plasmid pPA415. This plasmid was next transformed in B. subtilis 1A747 selecting for spectinomycin-resistance to integrate the P$_{ilvB*}$-lacZ fusion into the amyE chromosomal locus, generating strain PA431.

Plasmid pPA415 was further modified to contain mRNA stabilizing elements. To achieve this, this plasmid was digested with PshAI/NheI to release the ilv-leu leader region from the remainder of the vector sequences, ilvB native promoter region and upstream regions, and the lacZ structural gene segment (i.e. backbone fragment). This backbone DNA fragment was purified and ligated to sequences containing the B. subtilis cggR-gapA region that harbors an mRNA stabilizing DNA sequence (i.e. stabilizing element, Meinken et al., 2003, Microbiology 149: 751-76). This fragment was PCR amplified from B. subtilis 168 by using primer pair CggR-Loop+/CggRLoop- (Table 3), purified and digested with PshAI and NheI. The ligated DNA was transformed into E. coli competent cells selecting for ampicillin-resistance. This resulted in plasmid pPA422, in which the untranslated leader region between the ilvB promoter and the lacZ reporter gene was replaced by the cggR-gapA RNA stabilizing element (i.e. P$_{ilvΩcggR-gapA}$-lacZ). To insert the P$_{ilvΩcggR-gapA}$-lacZ cassette into the amyE chromosomal locus of B. subtilis, pPA422 plasmid DNA was then transformed into 1A747, selecting for spectinomycin-resistance. This yielded strain PA432. In standard ONPG assays developed with exponentially grown shake flask cultures containing minimal medium, strain PA432 produced 7-fold higher β-galactosidase levels than the isogenic strain PA431 containing the wild type promoter fusion (i.e. P$_{ilvB*}$-lacZ) without the cggR-gapA intergenic region.

TABLE 3

List of primers used to engineer microorganisms overproducing the LacZ protein under control of naturally occurring and not modified promoters.

| Primer | ID No. | Sequence |
|---|---|---|
| Pilv+ | 25 | 5'-GGCGTAATATGAGTTCAACAAAAGACAAATG TCAGCTTCAC-3' |
| Pilv- | 26 | 5'-CCTGTACATTAGTCCCCATGCTAGCTCCTCC TTTTGGATTTTCATCC-3' |
| PilvUP2+ | 27 | 5'-CTTTGAATTCGCAAGATATCATTAATGTAT GCC-3' |
| PilvUP+ | 28 | 5'-GCAAGATATCATTAATGTATGCC-3' |
| CggRLoop+ | 29 | 5'-GACATAGACGCCAGTCCCGATATTATTGCGG TAGC-3' |
| CggRLoop- | 30 | 5'-AATTAGCTAGCTCCTCCTTTTGGATCCTTTA AATAAGTGAGAGATATTTATATTGAGGG-3' |

Example IV

Strains Expressing the ilvBNC-leuABCD Operon Using its Native Promoter and an Exogenous mRNA Stabilizing Element with the 5' Leader Region can Achieve Similar Protein Levels as Strains Containing the ilvBNC-leuABCD Operon Under Transcription Control of a Constitutively Strong Exogenous Promoter.

To replace the native ilvB promoter with strong constitutive promoters or to introduce an mRNA stabilizing element between the native ilvB promoter region and the ilvB structural gene, a deletion of the native ilvB promoter region (P$_{ilvB}$) was first constructed as follows. A plasmid containing a chloramphenicol (cat)-resistance gene cassette flanked by B. subtilis chromosomal sections upstream and downstream of P$_{ilvB}$ was first constructed. To achieve this, a DNA fragment containing the 5' end of the ysnD gene (located upstream of the P$_{ilvB}$ promoter) was synthesized by PCR using from B. subtilis 168 chromosomal DNA as template and primers ysnD3- and ysnD+ (Table 4). A second PCR-generated fragment including a cat resistance-encoding gene was prepared using primers ilvBCat+ and ilvBCat- (Table 4) and plasmid pDG1661 (Guerout-Fleury et al. 1996, Gene 57-61) as template. This fragment overlaps the 3' end of the ysnD-containing PCR fragment. After purification, both PCR fragments were used as template in a third PCR reaction with primers ilvBCat+ and ysnD3-, yielding an ysdD'-cat fragment. A fourth PCR reaction was used to amplify the 5' end of the ilvB structural gene, which is downstream of P$_{ilvB}$. Thus, a PCR product was obtained from B. subtilis 168 chromosomal DNA by the use of primers ilvB+ and ilvB- (Table 4). This ilvB' fragment was cloned by the pCXLTOPO kit (Invitrogen) following manufacturer's instructions. The cloned fragment was subcloned into pUC19 (New England Biolabs) as a KpnI/SacI fragment. After its integrity was confirmed by restriction analysis, the ysnD'-cat fragment described above was inserted (using BamHI/KpnI sites) upstream of the ilvB' segment yielding the final plasmid pPA401. This plasmid was engineered in such a way that the cat gene sequences could be removed from the ysnD'-cat-ilvB' cassette by KpnI/MluI digestion and replaced by any other DNA element. Plasmid pPA401 was then transformed into a *B. subtilis* prototrophic wild-type strain (1A747) and into a pantothenate producer (PA73), selecting for chloramphenicol resistance. Cm$^r$ colonies were found to be an Ilv$^-$ auxotroph (i.e. bacteria that fail to grow on minimal medium without the addition of valine, leucine, and isoleucine amino acids). The resulting strains were named PA401 ($\Delta$ilv$_p$::cat) and PA441 (P$_{15}$ panBCD P$_{15}$panE P$_{26}$ ilvD $\Delta$ilv$_p$::cat).

To generate a strain containing an ilv-leu operon under the control of its native promoter but including a modified leader region, a DNA fragment containing the P$_{ilv\Omega cggR-gapA}$ cassette was amplified by PCR from plasmid pPA422 (see above) with primers PilvUP3+ and CggRLoop2- and pPA422 plasmid DNA as template (see above). The thus generated PCR fragment was digested with KpnI/MluI and ligated to a purified KpnI/MluI cat-free fragment of pPA401 (i.e. a DNA fragment with the structure, 5'-KpnI-ysnD-vector replication sequences-ilvB'-MluI-3'). The ligation mixture was directly transformed into PA441 and colonies selected for growth on minimal medium without supplementation with Ile, Val, or Leu amino acids. Many Ilv$^+$ colonies were obtained and the genetic background of several was confirmed by PCR. In addition these Ilv$^+$ PCR$^+$ colonies were also sensitive to chloramphenicol (Cm$^s$) as expected of replacement of the cat gene with the P$_{ilvB}$ promoter-mRNA stabilizing element region. One Ilv$^+$ PCR$^+$ Cm$^s$ colony was saved (PA445) for further study.

To generate strains containing an ilv-leu operon under the control of SP01-26 (P$_{26}$), a DNA fragment which contained a P$_{26}$ promoter was first PCR amplified using primers P26+1 and P26- and pUC19SP01-26 plasmid DNA as template. The resulting DNA product was digested with KpnI/MluI and ligated to a purified KpnI/MluI cat-free fragment of pPA401 (i.e. a DNA fragment with the strict, 5'-KpnI-ysnD-vector replication sequences-ilvB'-MluI-3'). The ligation mixture was directly transformed into PA401 ($\Delta$ilv$_p$::cat) and colonies selected for growth on minimal medium without supplementation with Ile, Val, or Leu. Many Ilv$^+$ colonies were obtained and the genetic background of several was confirmed by PCR. In addition these Ilv$^+$ PCR$^+$ colonies were also sensitive to chloramphenicol (Cm$^s$) as expected of replacement of the cat gene with the cggR-modified P$_{ilvB}$ promoter region. One Ilv$^+$ PCR$^+$ Cm$^s$ colonies was saved and named PA402. DNA sequencing confirmed the presence of a modified ilv-leu operon in which the cggR-gapA mRNA stabilizing element was inserted downstream of the ilvB promoter region (i.e. P$_{ilv\Omega cggR-gapA}$ ilvBNC-leuABCD). The P$_{ilv\Omega cggR-gapA}$ ilvBNC-leuABCD operon was next transferred to the pantothenate-production strain PA73 using PBS1 generalized transduction in the following way: A PBS1 phage lysate was prepared using PA402 and a method known to those skilled in the art. This lysate was used to infect PA441 and colonies selected for growth on minimal medium without supplementation with Ile, Val, or Leu. Many Ilv$^+$ colonies were obtained and the genetic background of several was confirmed by PCR. In addition these Ilv$^+$ PCR$^+$ colonies were also sensitive to chloramphenicol (Cm$^s$) as expected of replacement of the cat gene with the P$_{ilvB}$ promoter-mRNA stabilizing element region. One Ilv$^+$ PCR$^+$ Cm$^S$ colony was saved (PA444) for further study.

Two dimensional protein gels were used to compare the level of protein synthesis of ilv- and leu-encoded genes between strain PA444 containing the strong constitutive SP01-26 promoter and wild-type 5' untranslated leader region, and strain PA445 containing the wild-type promoter region and a 5' untranslated leader region modified with the cggR-gapA RNA stabilizing element, using methods known by those skilled in the art. Significant increases in protein levels were observed in both PA444 and PA445 with respect to the parental PA73 strain:
PA444-IlvB 56%, IlvC 473%, LeuA 271%, LeuB 579%, LeuC 153%, and LeuD 306%;
PA445, IlvB 60%, IlvC 648%, LeuA 274%, LeuB 499%, LeuC 195%, and LeuD 523%.

It can be concluded from these results that the increase in protein levels encoded by genes from the ilv-leu operon was within the same range for both PA444 and PA445 strains.

TABLE 4

List of primers used to engineer the ilvBNC-leuABCD operon in pantothenate overproducer strains.

| Primer | ID No. | Sequence |
|---|---|---|
| ysnD3- | 31 | 5'-AGTAGGATCCAGAGGGAGTGGTTAACG GGC-3' |
| ysnD+ | 32 | 5'-TATGAGATAATGCCGACTGTACTTACGCGTC GCCGCTTTGGACGCAGTGTC-3' |
| ilvBCat+ | 33 | 5'-CCACCTGTACATTAGTCCCCATATGAGTTTC ACCTCCTTACTCGAGGTACCCGAAAATTGGATAA AGTGGG-3' |
| ilvBCat- | 34 | 5'-GACACTGCGTCCAAAGCGGCGACGCGTAAGT ACAGTCGGCATTATCTCATA-3' |
| ilvB+ | 35 | 5'-CCCACTTTATCCAATTTTCGGGTACCTCGAG TAAGGAGGTGAAACTCATATGGGGACTAATGTAC AGGTGG-3' |
| ilvB- | 36 | 5'-TTTGAGCTCGGTTTAACACCCCGGAG CGG-3' |
| PilvUP3+ | 37 | 5'-CTTTACGCGTCAAGATATCATTAATGTAT GCC-3' |
| CggRLoop2- | 38 | 5'-TTTTGGTACCTTTAAATAAGTGAGAGATATT TATATTGAGGG-3' |
| P26 + 1 | 39 | 5'-GGGTTACGCGTGGCCGCTAACTACACTAACA GC-3' |
| P26- | 40 | 5'-GGGTTGGTACCTTTAATTCTCGAGTGTTA AG-3' |

Example V

Introduction of Endogenous mRNA Stabilizing Elements are Able to Increase Transcript Abundance of mRNA Encoded by Native Promoters PA444 and PA455 are isogenic strains except for the presence of different DNA elements controlling transcription of the ilv-leu operon: PA444 contains the strong constitutive SP01-26 promoter and wild-type 5' untranslated leader region, and PA445 contains the wild-type promoter and a modified 5' untranslated leader region with the cggR-gapA RNA stabilizing element. To analyze the effect of the two different DNA elements on transcription of the ilv-leu operon, standard Northern blots were used to analyze the mRNA transcript profiles of both strains. Labeled antisense mRNA probes were generated to the ilvB, ilvC, and leuD genes from PCR fragments obtained with primers IlvBFor/IlvBRev (IlvB probe), IlvCFor/IlvCRev (IlvC probe), and LeuDFor/LeuDRev (LeuD probe) (Table 5), and hybridized separately to total RNA separated on denaturing agarose gels under standard conditions. Results showed that that the two strains generated different transcript profiles. A high abundance 3.5 kb mRNA species that hybridized to both the ilvB and ilvC probes, but not to the leuD probe, was detected in PA445 total RNA, but not in PA444 total RNA. According to Mäder et al, this 3.5 kb transcript encompasses the ilvB, ilvN, and ilvC genes and is not detected from total RNA from wild type bacteria (Mäder et al., 2004, J. Bacteriol. 186:2240-2252). Moreover since this RNA species is not detected in PA445, anyone skilled in the art will recognize that the increase abundance of this mRNA species was caused by increasing the stability of the mRNA message by the cggR-gapA DNA element and not by increasing the level of transcription.

Likewise, the abundance of two additional transcripts of 8.5 kb and 2.5 kb was greater in strain PA445 than PA444. Since the 2.5 kb transcript hybridized to the ilvB probe but not to the ilvC and leuD probes, it can be concluded that this mRNA encompasses the ilvB and ilvN genes. Since the 8.5 kb transcript hybridized to the leuD probes, it must encompass the entire ilv-leu operon. Using the same rationale above, the greater abundance of these two RNA species in PA445 than in PA444 can only be attributable to their higher stability, which in turn must come as a consequence of the introduction of the cggR-gapA element into 5' leader sequence of the ilv-leu operon.

TABLE 5

List of primers used to obtain DNA fragments encoding RNA antisense to the IlvB, IlvC or leuC genes.

| Primer | ID No. | Sequence |
|---|---|---|
| IlvBFor | 41 | 5'-TGTACACAGACGATGAGC-3' |
| IlvBRev | 42 | 5'-CTAATACGACTCACTATAGGGAGTTAGATTCT GAATAACGTTCTT-3' |
| IlvCFor | 43 | 5'-AGAGAACGTATTGGCTGG-3' |
| IlvCRev | 44 | 5'-CTAATACGACTCACTATAGGGAGCCACTACTT CGATTTGATGTTC-3' |
| LeuDFor | 45 | 5'-GGTTCTTCCTGTCGATTC-3' |
| LeuDRev | 46 | 5'-CTAATACGACTCACTATAGGGAGGCTGATTTT CAAGGTCAACAGT-3' |

Example VI

Increasing The Level of Proteins Encoded by The ilvBNC-leuABCD Operon by Use of mRNA stabilizing elements, increases the production of pantothenate in B. subtilis Cells Strains PA73, PA444, and PA445 were evaluated for pantothenate production in shake flask cultures containing VFB MMGT minimal medium and grown for 48 hours. HPLC analysis of cell-free supernatants prepared from these shake flask cultures revealed the presence of pantothenate at the following levels:
PA73, 550 mg/l;
PA444, 150 mg/l;
PA445, 750 mg/l.

Results showed that increasing the transcription level of the ilvBNC-leuABCD operon by a constitutive strong promoter yielded a production of pantothenate lower than the parental strain. Conversely, increasing the stability of the ilvBNC-leuABCD mRNA transcripts by the cggR-gapA stabilizing element led to pantothenate titers higher than that produced by the PA73 parental strain. Since the protein content was shown to be almost identical in both PA444 and PA445, increasing the stability of the ilvBNC-leuABCD transcripts using the cggR-gapA stabilizing was more effective in enhancing pantothenate production than increasing the level of transcription by use of the constitutive SPO1 promoter. In good agreement with this conclusion, strain PA444 grew slower than PA445 and had a higher rate of cell lysis during prolonged growth.

Example VII

Stabilization of mRNA is Independent of RNase E Activity in B. Subtilis

Strain B. subtilis 168 has been described to contain two genes (ymfA and ykqC) encoding supposedly functional homologues of E. coli RNase E. Strain SSB348 is a derivative of wild type B. subtilis 168 in which gene ymfA is deleted and ykqC expression is placed under the control of an IPTG (isopropylgalactopiranoside)-inducible promoter ($P_{spac}$) (Even et al., 2005, Nucleic Acids Res 33:2141). Strain SSB348 was transformed with DNA extracted from strains PA431, PA432, PA494, and PA517 to yield strains PA602 (ilvB-lacZ fusion expressed under control of native ilvB promoter signals), PA603 (ilvB-lacZ fusion expressed as stabilized transcript by addition of the cggR-gapA mRNA stabilizing element at the 5' end expressed under control of native ilvB promoter signals), PA604 (ilvB-lacZ fusion expressed as stabilized transcript by addition of the cggR-gapA mRNA stabilizing element at the 5' end expressed under control of native ilvB promoter signals) and PA605 (ilvD-lacZ fusion transcribed under control of native promoter signals ilvD gene as stabilized transcript by incorporating the hrcA-grpE stabilizing element at the 5' end), respectively. Each strain was grown in 25 ml shake flask cultures for 18 hours at 37° C., and β-galactosidase levels were measured using standard (ONPG assay) methods; these results are summarized in Table 6. In each strain, no difference in α-galactosidase levels was observed when cells were grown in the presence or absence of IPTG induction. These results demonstrate that the activities encoded by the genes ymfA and ykqC are not required for the function of mRNA stabilizing elements in B. subtilis.

TABLE 6

ONPG assay results obtained from experiments developed with strains PA602, PA603, PA604 and PA605.

| | β-galactosidase levels (Miller units) | |
|---|---|---|
| Strain | +IPTG | −IPTG |
| PA602 | 44 | 34 |
| PA603 | 490 | 570 |
| PA604 | 42 | 36 |
| PA605 | 120 | 130 |

Example VIII

The Effects of the Secondary Structure of the Stabilizing Elements and the Length of Unpaired 5' Sequence on the Enhanced Protein Synthesis Mediated by mRNA Stabilization Sharp and Bechhofer (2005, Molecular Microbiology 57:484-495) demonstrated that for the efficient mRNA stabilization in *B. subtilis* (i) the 5'-terminal secondary structure has to have a free energy ($\Delta G$) under a minimal value (−2.8 and −4.7 kcal/mol) and (ii) located less than 4 and 7 unpaired nucleotides (nts) from the 5'-end of the transcript. The presence of four unpaired nucleotides (at the ermC stabilizing element) and seven unpaired nucleotides (at the SP82 stabilizing element) resulted in a complete loss of stabilization.

In Example III it was shown that PA432 ($P_{ilv\Omega cggR-gapA}$-lacZ) containing the cggR-gapA mRNA stabilizing element upstream of the lacZ reporter gene produced 7-fold more β-galactosidase than the isogenic strain PA431 containing only the wild type ilvB promoter lacZ fusion ($P_{ilvB}$-lacZ). In PA432 the two stabilizing stem-loop structure of the cggR-gapA mRNA stabilizing element was located 93 nucleotides downstream of the +1 transcriptional start site of the lacZ transcript. To predict the secondary structure of the cggR-gapA stabilizing element and to determine the length of unpaired sequence at the 5'-end of the transcript, the leader region of the lacZ mRNA in PA432 was analyzed using the mfold structure prediction program of Zuker (2003, Nucleic Acids Research 31:3406-3415). The 260-nt leader region (from +1 transcriptional start until, but not including, the spoVG RBS sequence for the translation of lacZ) contained 8 unpaired nucleotides at the 5'-end of the transcript followed by a very weak stem-loop ($\Delta G$=−0.5 kcal/mol). The first stabilizing stem-loop (SL1) of the cggR-gapA stabilizing element (predicted structure in Ludwig et al., 2001, Molecular Microbiology 41:409-422) was truncated in PA432. The truncated SL1 (SL1T) had features of $\Delta G$=−4.8 kcal/mol; 8 nts in the double-stranded stem; 1 nt bulge loop; and 3 nts hairpin loop.

Using the mfold program it was predicted that the SL1 stabilizing stem-loop ($\Delta G$=−11.6 kcal/mol; 11 nts in the double-stranded stem; 2 nts bulge loop; and 3 nts hairpin loop) could be restored by removing 75 nts (+19 nt to +93 nt) from the 277-nt leader region of the lacZ mRNA in PA432 (SEQ ID No. 47). To test whether SL1 confers higher levels of mRNA stabilization than SL1T, a leader deletion derivative, called cggR-gapA#10 was constructed upstream of lacZ. First, 130-bp PCR product containing the cggR-gapA stabilizing element was amplified with primers GAP#10-FOR and GAP#10-REV (Table 7) using pPA422 as a template DNA. The PCR product was digested with PshAI and NheI enzymes and cloned into the PshAI and NheI sites in pPA415 plasmid. After transformation of *E. coli* TOP10, Amp$^r$ and Spec$^r$ transformants were selected. The resulting pBest10 was next transformed into *B. subtilis* 1A747 selecting for Spec$^r$ to integrate the $P_{ilv\Omega cggR-gapA\#10}$-lacZ fusion into the amyE chromosomal locus, generating strain BE10. In shake flask assays cultures were grown in both LB medium and minimal medium, and the BE10 ($P_{ilv\Omega cggR-gapA\#10}$-lacZ) strain produced similar levels of β-galactosidase as the isogenic strain PA432 ($P_{ilv\Omega cggR-gapA}$-lacZ). The data indicated that efficient mRNA stabilization mediated by the cggR-gapA element was independent on (i) the distance from 5'-terminus to the stabilizing sequence (19 nts vs. 93 nts); and (ii) the strength of the secondary structure (SL1T vs. SL1 stabilizing stem-loop).

To study the effect of unpaired 5'-terminal nucleotides 39 nts (+180 nt to +218 nt) was removed from the 277-nt leader region of the lacZ mRNA in PA432 (SEQ ID No. 47) and the structure of the 238-nt leader deletion derivative, called cggR-gapA#14, was predicted using the mfold program. The 277-nt original leader sequence contained 8 unpaired nucleotides, and the cggR-gapA#14 deletion leader contained 16 unpaired nucleotides at the 5'-end of the transcript. To construct a *B. subtilis* mutant carrying the cggR-gapA#14 deletion leader, first a 39-bp fragment was removed with BamHI digestion between the stabilizing element and the lacZ gene in the pPA422 plasmid. After self-ligation of the digested plasmid and transformation of *E. coli* TOP 10, Amp$^r$ and Spec$^r$ transformants were selected. The resulting pBest14 was next transformed into *B. subtilis* 1A747 selecting for Spec$^r$ to integrate the $P_{ilv\Omega cggR-gapA\#14}$-lacZ fusion into the amyE chromosomal locus, generating strain BE14. Bacterial cultures were grown in both LB medium and minimal medium in shake flask assays and the BE14 ($P_{ilv\Omega cggR-gapA\#14}$-lacZ) strain produced similar levels of β-galactosidase as the isogenic strain PA432 ($P_{ilv\Omega cggR-gapA}$-lacZ). The data indicated that efficient mRNA stabilization was achieved when 16 unpaired nucleotides were at the 5'-end of the lacZ transcript in the BE14 strain.

TABLE 7

List of primers used to study the effect of the secondary structures of the cggR-gapA stabilizing element and the length of unpaired 5' sequence.

| Primer | ID No. | Sequence |
| --- | --- | --- |
| GAP#10-FOR | 48 | 5'-ACAAAGACAACAGTCCGGTTCTCGTCACA GACGA-3' |
| GAP#10-REV | 49 | 5'-CCCATGCTAGCTCCTCCTTTTGGATCCTT TAAATAAG-3' |

The invention claimed is:

1. A method for the production of a desired chemical compound in a microorganism, wherein the stability of an mRNA transcript from a gene involved in the biosynthesis of said compound is increased by the introduction of a DNA sequence compared to the stability of said mRNA without said introduced DNA sequence wherein the DNA sequence is introduced seven or more nucleotides downstream of the transcription start of said gene and wherein said DNA sequence is a chromosomal nucleotide DNA sequence of the cggR-gapA intercistronic region of *Bacillus subtilis* and consists of at least 15 nucleotides forming one or more stem loop secondary structures showing (i) a double-stranded stem structure of at least 6 base pairs and a hairpin loop structure of 3-30 nucleotides and (ii) a calculated thermodynamic stability (ΔG) of said structure of −2.8 kcal/mol or lower.

2. A method of claim 1, wherein the microorganism is of the genus *Bacillus*.

3. A method of claim 1, wherein the microorganism is of the species *Bacillus subtilis*.

4. The method of claim 1, wherein the DNA sequence is a sequence occurring naturally which is located 10 nucleotides downstream of the stop codon of the cggR gene, of *Bacillus subtilis*, represented by SEQ ID No. 1 or a part thereof.

5. The method of claim 4, wherein the DNA sequence is SEQ ID No. 2.

6. A method for the production of a desired chemical compound selected from vitamins, enzymes, amino acids or nucleotides in a microorganism comprising the steps of:
(a) introduction of a chromosomal nucleotide DNA sequence seven or more nucleotides downstream of the transcription start of a gene involved in the biosynthesis of vitamins, enzymes, amino acids or nucleotides, said chromosomal nucleotide sequence which is a contiguous sequence occurring in the cggR-gapA intercistronic region of *Bacillus subtilis* that consists of at least 15 nucleotides forming one or more stem loop secondary structures showing (i) a double-stranded stem structure of at least 6 base pairs and a hairpin loop structure of 3-30 nucleotides and (ii) a calculated thermodynamic stability (ΔG) of said structure of −2.8 kcal/mol or lower;
(b) transcription of mRNA from said gene leading to RNA sequence containing a stabilizing element at the 5' end, and
(c) optionally isolating said chemical compound.

7. A method according to claim 6, wherein the microorganism is selected from *Bacillus*.

8. The method according to claim 6, wherein the chemical compound is pantothenic acid.

9. The method according to claim 6, wherein the gene comprises the ilv-operon and the mRNA transcribed from the ilv-operon is stabilized.

* * * * *